United States Patent
Enz et al.

(10) Patent No.: US 11,969,323 B2
(45) Date of Patent: Apr. 30, 2024

(54) ABSORBENT ARTICLE WITH POCKET DIVIDING FRONT AND REAR REGIONS

(71) Applicant: Kimberly-Clark Worldwide, Inc., Neenah, WI (US)

(72) Inventors: David J. Enz, Neenah, WI (US); Patrick R. Lord, Appleton, WI (US); Kyle M. Barriger, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1315 days.

(21) Appl. No.: 16/480,613

(22) PCT Filed: Jun. 23, 2017

(86) PCT No.: PCT/US2017/039086
§ 371 (c)(1),
(2) Date: Jul. 24, 2019

(87) PCT Pub. No.: WO2018/144058
PCT Pub. Date: Aug. 9, 2018

(65) Prior Publication Data
US 2020/0022848 A1   Jan. 23, 2020

(51) Int. Cl.
*A61F 13/495* (2006.01)
*A61F 13/15* (2006.01)
(Continued)

(52) U.S. Cl.
CPC ........ *A61F 13/495* (2013.01); *A61F 13/4942* (2013.01); *A61F 13/5116* (2013.01);
(Continued)

(58) Field of Classification Search
CPC ................ A61F 13/4942; A61F 13/495; A61F 13/5116; A61F 13/513; A61F 2013/15512;
(Continued)

(56) References Cited

U.S. PATENT DOCUMENTS

| 4,753,646 A | 6/1988 | Enloe |
| 5,269,775 A | 12/1993 | Freeland et al. |

(Continued)

FOREIGN PATENT DOCUMENTS

| CN | 1143904 A | 2/1997 |
| CN | 1235012 A | 11/1999 |

(Continued)

OTHER PUBLICATIONS

Co-pending U.S. Appl. No. 16/480,543, filed Jul. 24, 2019, by Enz et al. for "Absorbent Article with Pocket Dividing Front and Rear Regions."

*Primary Examiner* — Michele Kidwell
(74) *Attorney, Agent, or Firm* — KIMBERLY-CLARK WORLDWIDE, INC.

(57) ABSTRACT

Absorbent articles of the present disclosure may be constructed with a secondary liner sheet placed on top of a body facing liner of the articles configured to form a pocket. The pocket provides a barrier, thereby separating a front region of the absorbent articles from a rear region. In this manner, the absorbent articles of the present disclosure may reduce the spread of bodily exudates throughout the articles. The reduced spreading of exudates may help to keep skin healthy by reducing the amount of skin exposed to the skin irritants within the exudates and/or by preventing additional skin irritants from being created by preventing the mixing of BM and urine, at least in proximity to the skin of the wearer.

18 Claims, 14 Drawing Sheets

(51) Int. Cl.
  *A61F 13/494* (2006.01)
  *A61F 13/511* (2006.01)
  *A61F 13/513* (2006.01)
  *A61F 13/58* (2006.01)

(52) U.S. Cl.
  CPC ............... *A61F 2013/15512* (2013.01); *A61F 2013/49493* (2013.01); *A61F 2013/4951* (2013.01); *A61F 2013/4953* (2013.01); *A61F 2013/4956* (2013.01); *A61F 2013/4958* (2013.01); *A61F 13/513* (2013.01); *A61F 2013/586* (2013.01)

(58) Field of Classification Search
  CPC .... A61F 2013/49493; A61F 2013/4951; A61F 2013/4953; A61F 2013/4956; A61F 2013/4958; A61F 2013/586
  See application file for complete search history.

(56) References Cited

U.S. PATENT DOCUMENTS

| | | | |
|---|---|---|---|
| 5,531,730 | A | 7/1996 | Dreier |
| 5,576,091 | A | 11/1996 | Zajaczkowski et al. |
| 5,766,411 | A | 6/1998 | Wilson |
| 5,810,799 | A | 9/1998 | Slater |
| 5,938,652 | A | 8/1999 | Sauer |
| 5,968,028 | A | 10/1999 | Roe et al. |
| 6,010,490 | A | 1/2000 | Freeland et al. |
| 6,315,764 | B1 | 11/2001 | Faulks et al. |
| 6,450,998 | B1 | 9/2002 | Otsubo et al. |
| 6,685,689 | B1 | 2/2004 | Rönnberg |
| 6,699,228 | B1 | 3/2004 | Chmielewski et al. |
| 6,749,593 | B1 | 6/2004 | Flohr et al. |
| 6,786,895 | B1 | 9/2004 | Schmitz |
| 6,896,668 | B2 | 5/2005 | Kashiwagi et al. |
| 6,921,394 | B2 | 7/2005 | Sayama et al. |
| 7,037,298 | B2 | 5/2006 | Ohshima et al. |
| 7,252,657 | B2 | 8/2007 | Mishima et al. |
| 7,470,264 | B2 | 12/2008 | Mishima et al. |
| 7,563,257 | B2 | 7/2009 | Nakajima et al. |
| 7,666,173 | B2 | 2/2010 | Mishima et al. |
| 7,722,587 | B2 | 5/2010 | Suzuki et al. |
| 7,755,888 | B2 | 7/2010 | Sun |
| 7,763,002 | B2 | 7/2010 | Otsubo |
| 7,766,888 | B2 | 8/2010 | Mishima et al. |
| 7,812,213 | B2 | 10/2010 | Doverbo et al. |
| 7,867,210 | B2 | 1/2011 | Mori et al. |
| 8,016,803 | B2 | 9/2011 | Mueller et al. |
| 8,029,486 | B2 | 10/2011 | Nakajima et al. |
| 8,157,778 | B2 | 4/2012 | Moriya et al. |
| 8,197,457 | B2 | 6/2012 | Suzuki et al. |
| 8,246,595 | B2 | 8/2012 | Carlson et al. |
| 8,298,204 | B2 | 10/2012 | Otsubo |
| 8,377,025 | B2 | 2/2013 | Nakajima et al. |
| 8,679,084 | B2 | 3/2014 | Kurihara |
| 8,728,050 | B2 | 5/2014 | Nitta et al. |
| 8,889,946 | B2 | 11/2014 | Hermansson et al. |
| 9,050,218 | B2 | 6/2015 | Martynus et al. |
| 9,050,219 | B2 | 6/2015 | Martynus et al. |
| 9,084,698 | B2 | 7/2015 | Ichikawa et al. |
| 9,314,382 | B2 | 4/2016 | Zilm |
| 9,456,935 | B2 | 10/2016 | Nelson, II et al. |
| 11,712,377 | B2* | 8/2023 | Enz .............. A61F 13/495 604/385.19 |
| 2003/0045853 | A1 | 3/2003 | Sauer |
| 2003/0083631 | A1 | 5/2003 | Chen et al. |
| 2004/0116883 | A1 | 6/2004 | Krautkramer et al. |
| 2005/0228358 | A1 | 10/2005 | Mishima et al. |
| 2005/0267436 | A1* | 12/2005 | Mishima .......... A61F 13/4915 604/385.19 |
| 2006/0184151 | A1 | 8/2006 | Onishi et al. |
| 2006/0271005 | A1 | 11/2006 | LaVon et al. |
| 2006/0287635 | A1 | 12/2006 | Angel |
| 2010/0274209 | A1 | 10/2010 | Roe et al. |
| 2011/0106040 | A1 | 5/2011 | Minato et al. |
| 2012/0022489 | A1 | 1/2012 | Wakasugi et al. |
| 2012/0040039 | A1 | 2/2012 | Alkmin et al. |
| 2013/0012898 | A1 | 1/2013 | Bergendahl et al. |
| 2014/0221955 | A1 | 8/2014 | Brown et al. |
| 2014/0221957 | A1* | 8/2014 | Martynus .......... A61F 13/49017 604/385.28 |
| 2014/0296809 | A1 | 10/2014 | Hammons et al. |
| 2015/0032071 | A1 | 1/2015 | Suzuki et al. |
| 2015/0045759 | A1 | 2/2015 | Martynus et al. |
| 2015/0057631 | A1 | 2/2015 | Dieringer et al. |
| 2015/0164706 | A1 | 6/2015 | Ben-Natan et al. |
| 2015/0209195 | A1 | 7/2015 | Martynus et al. |
| 2015/0223995 | A1 | 8/2015 | Martynus et al. |
| 2015/0223996 | A1 | 8/2015 | Martynus et al. |
| 2015/0257946 | A1 | 9/2015 | Martynus et al. |
| 2016/0256332 | A1 | 9/2016 | Brown et al. |
| 2016/0256333 | A1 | 9/2016 | Brown et al. |
| 2016/0278994 | A1 | 9/2016 | Martynus et al. |

FOREIGN PATENT DOCUMENTS

| | | |
|---|---|---|
| CN | 1372874 A | 10/2002 |
| CN | 1539391 A | 10/2004 |
| CN | 1572267 A | 2/2005 |
| CN | 104822352 A | 8/2015 |
| EP | 0091412 B1 | 5/1987 |
| JP | 3186261 A | 8/1991 |
| JP | 8196565 A | 8/1996 |
| JP | 2003144488 A | 5/2003 |
| KR | 20020062695 A | 7/2002 |
| KR | 20070013398 A | 1/2007 |
| WO | 9963921 A1 | 12/1999 |
| WO | 0106974 A1 | 2/2001 |
| WO | 15005166 A1 | 1/2015 |
| WO | 15055695 A1 | 4/2015 |
| WO | 15055696 A1 | 4/2015 |
| WO | 15198928 A1 | 12/2015 |
| WO | 15198929 A1 | 12/2015 |
| WO | 16159978 A1 | 10/2016 |
| WO | 18143921 A1 | 8/2018 |
| WO | 19027406 A1 | 2/2019 |

\* cited by examiner

ABSORBENT ARTICLE WITH POCKET DIVIDING FRONT AND REAR REGIONS

TECHNICAL FIELD

The present disclosure is directed to diapers, including infant diapers, training pants, adult incontinence articles and the like wherein a secondary liner sheet and body facing liner are uniquely bonded to containment flaps to form a pocket thus enabling enhanced absorption and containment of bodily waste within the absorbent article.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

Another important emphasis of some absorbent articles is to contain exudates within particular regions of the articles. Containing exudates within particular regions, or even otherwise reducing the spreading of exudates within an absorbent article, can help to keep the skin of a wearer healthy. For instance, bowl movement (BM) exudates may contain skin irritants which can cause rashes or other skin conditions. Additionally, in some cases where BM mixes with urine, byproducts may be produced that irritate the skin. Accordingly, by helping to contain exudates within particular regions of the articles, or at least by reducing the spreading of BM within the articles, absorbent articles may help promote and maintain healthier skin.

SUMMARY OF THE DISCLOSURE

The absorbent articles disclosed herein are designed to contain exudates within particular regions of the articles or otherwise reduce the spreading of exudates throughout the articles. In at least some disclosed embodiments, absorbent articles of the present disclosure may contain a secondary liner sheet which forms a pocket which provides a barrier separating a front region of the absorbent articles from a rear region. The pocket may face the rear region of the absorbent article, thereby helping to prevent BM exudates from spreading forward and contacting the sensitive genital area of a wearer. In this manner, the articles of the present disclosure may help to increase functionality and performance of the absorbent article as well as to help maintain healthy skin of a wearer.

In a first embodiment, the absorbent articles of the present invention may contain a chassis extending in a longitudinal direction and having a longitudinal centerline and a lateral direction and having a lateral centerline, the chassis having a front waist region including a front waist edge, a rear waist region including a rear waist edge, and a crotch region extending between the front waist region and the rear waist region, and the chassis comprising: a garment facing outer cover, a body facing liner, an absorbent body disposed between the garment facing outer cover and the body facing liner; a pair of containment flaps extending between the front waist region and the rear waist region, each of the pair of containment flaps having distal edges and proximal edges; and a secondary liner sheet having a rear sheet edge, a front sheet edge, and longitudinally extending sheet side edges, wherein the secondary liner sheet is attached to each of the containment flaps along flap attachment regions disposed proximate the distal edges, wherein each of the flap attachment regions has a flap attachment region length, and wherein each of the flap attachment region lengths is between about 8% and about 16% of a total length of the absorbent article. A further embodiment may comprise a flap attachment region length that is more preferably from about 10% to 16% of the total length of the absorbent article.

In a second embodiment, an absorbent article according to any of the preceding embodiments, wherein the flap attachment region lengths are the same.

In a third embodiment, an absorbent article according to any of the preceding embodiments, wherein the secondary liner sheet is attached to each of the pair of containment flaps along longitudinally extending attachment regions disposed proximate the proximal edges.

In a fourth embodiment, an absorbent article according to any of the preceding embodiments, wherein the longitudinally extending attachment regions disposed proximate the proximal edges are second longitudinally extending attachment regions, and wherein each of the pair of containment flaps are attached to the body facing liner along first longitudinally extending attachment regions disposed proximate the proximal edges.

In a fifth embodiment, an absorbent article according to any of the preceding embodiments, wherein the second longitudinally extending attachment regions are disposed laterally closer to the longitudinal centerline than the first longitudinally extending attachment regions.

In a sixth embodiment, a chassis extending in a longitudinal direction and having a longitudinal centerline and a lateral direction and having a lateral centerline, the chassis having a front waist region including a front waist edge, a rear waist region including a rear waist edge, and a crotch region extending between the front waist region and the rear waist region, and the chassis comprising a garment facing outer cover, a body facing liner, an absorbent body disposed between the garment facing outer cover and the body facing liner; a pair of containment flaps extending between the front waist region and the rear waist region, each of the pair of containment flaps having distal edges and proximal edges; and a secondary liner sheet having a rear sheet edge, a front sheet edge, and longitudinally extending sheet side edges, wherein each of the pair of containment flaps are attached to the body facing liner along first longitudinally extending attachment regions disposed proximate the proximal edges, wherein the secondary liner sheet is attached to each of the containment flaps along flap attachment regions disposed proximate the distal edges, each of the flap attachment regions having a flap attachment region length and a flap attachment region height, the flap attachment region height being defined as a distance between one of the first longitudinally extending attachment regions and an edge of a flap attachment region most proximate a distal edge of a containment flap, wherein the secondary liner sheet is attached to the body facing liner through a liner attachment region and has a rear un-bonded region extending between the liner attachment region and the rear sheet edge, the rear un-bonded region having a rear un-bonded region length, and wherein the rear un-bonded region length is greater than the flap attachment region height.

In a seventh embodiment according to the sixth embodiment, wherein the rear un-bonded region is at least greater than 50% of the flap attachment region height plus the length of the attachment.

In an eighth embodiment, an absorbent article according to any of the preceding embodiments, wherein the rear un-bonded region length is greater than the sum of flap attachment region length and 50% of the flap attachment region height.

In a ninth embodiment, an absorbent article according to any of the preceding embodiments, wherein the rear un-bonded region length is less than the sum of the flap attachment region length and 150% of the flap attachment region height.

In a tenth embodiment, an absorbent article according to any of the preceding embodiments, wherein the rear un-bonded region length is greater than the sum of the flap attachment region length and 80% of the flap attachment region height.

In an eleventh embodiment, an absorbent article according to any of the preceding embodiments, wherein the rear un-bonded region length is less than the sum of the flap attachment region length and 120% of the flap attachment region height.

In a twelfth embodiment, wherein an absorbent article comprising a chassis extending in a longitudinal direction and having a longitudinal centerline and a lateral direction and having a lateral centerline, the chassis having a front waist region including a front waist edge, a rear waist region including a rear waist edge and a crotch region extending between the front waist region and the rear waist region, and the chassis comprising a garment facing outer cover, a body facing liner, an absorbent body disposed between the garment facing outer cover and the body facing liner; a pair of containment flaps extending between the front waste edge and the rear waste edge, each of the pair of containment flaps having distal edges and proximal edges; and a secondary liner sheet having a rear sheet edge, a front sheet edge, and longitudinally extending sheet side edges, wherein the secondary liner sheet is attached to the body facing liner through a liner attachment region, the liner attachment region having a liner attachment region front edge and a liner attachment region rear edge, wherein the liner attachment rear edge is disposed away from the front waist edge a distance greater than about 40% of a total length of the absorbent article.

In a thirteenth embodiment, an absorbent article according to the twelfth embodiment, wherein the liner attachment rear edge is disposed away from the front waist edge a distance greater than about 35% of the total length of the absorbent article.

In a fourteenth embodiment, an absorbent article according to any of the preceding embodiments, wherein the liner attachment rear edge is disposed away from the front waist edge a distance greater than about 25% of the total length of the absorbent article.

In a fifteenth embodiment, an absorbent article according to any of the preceding embodiments, wherein the liner attachment region has a liner attachment region length extending between the liner attachment region front edge and the liner attachment region rear edge, and wherein the liner attachment region length is between about 1% and about 15% of the total length of the absorbent article.

In a sixteenth embodiment, an absorbent article according to any of the preceding embodiments, wherein the liner attachment region has a liner attachment region length extending between the liner attachment region front edge and the liner attachment region rear edge, and wherein the liner attachment region length is between about 5% and about 15% of the total length of the absorbent article.

In a seventeenth embodiment, an absorbent article according to any of the preceding embodiments, wherein the secondary liner sheet is hydrophilic.

In an eighteenth embodiment, an absorbent article according to any of the preceding embodiments, wherein the liner attachment region is hydrophilic.

In another embodiment, an absorbent article according to any of the preceding embodiments, wherein the secondary liner sheet to body facing liner attachment should begin at a point of about 35% forward from the center axis of an absorbent article and continue for at least 75% of the total attached length between the body facing line and the secondary liner sheet.

In a further embodiment, an absorbent article according to any of the preceding embodiments, wherein the secondary liner sheet that forms the pocket may comprise a pocket material that has a 35 gsm spunbond, polypropylene material treated with surfactant with hexadot bond pattern, wherein the surfactant add on level is 0.7%.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
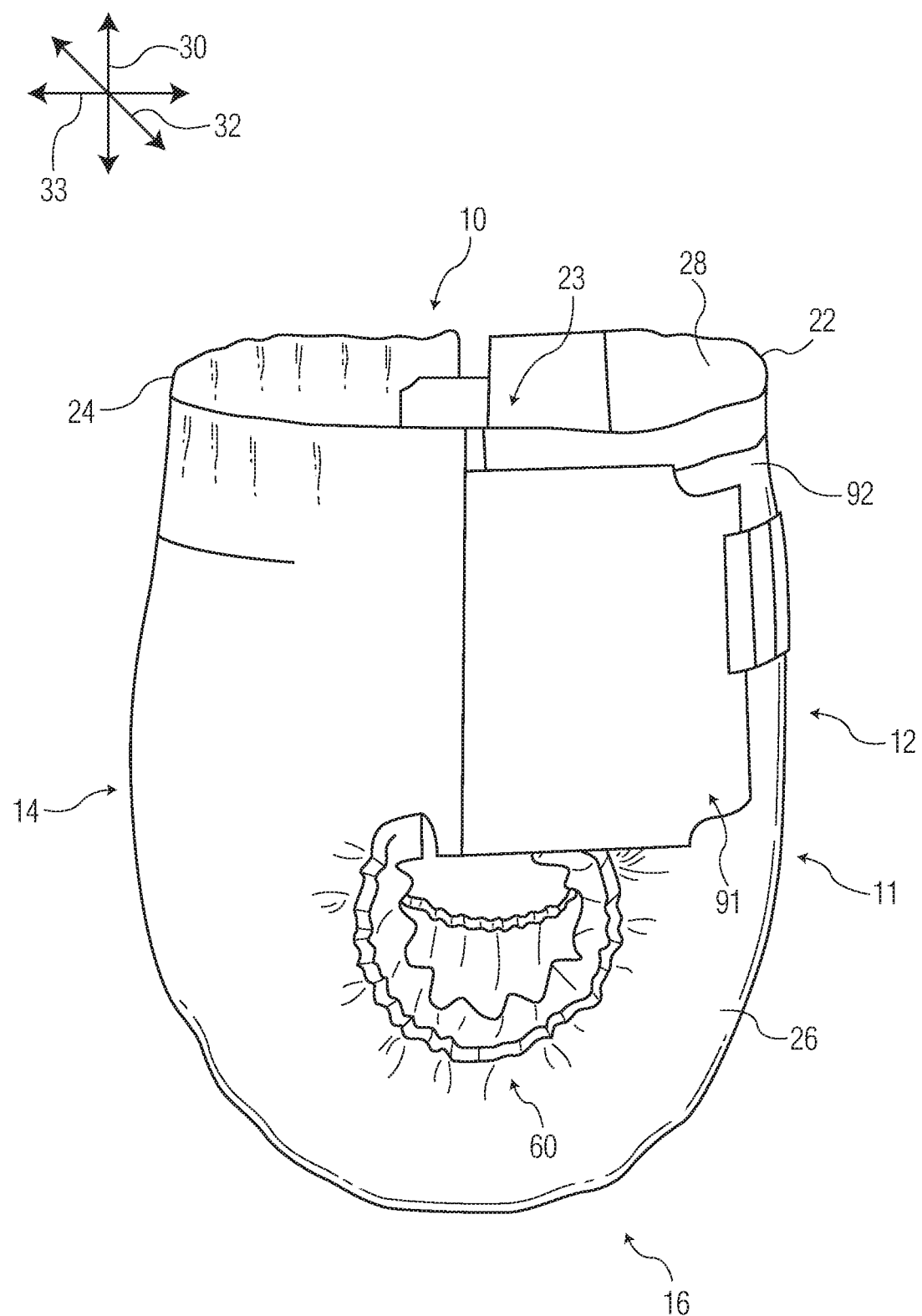
FIG. 1 perspective view of an absorbent article according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed towards the design of absorbent articles. More specifically, the disclosure is directed toward a design for bonding a secondary liner sheet and a bodying facing liner to containment flap(s) in a configuration which may help prevent skin irritation of a wearer.

Absorbent articles of the present disclosure may be constructed with a secondary liner sheet placed on top of a body facing liner of the articles configured to form a pocket. The pocket provides a barrier, thereby separating a front region of the absorbent articles from a rear region. In this manner, the absorbent articles of the present disclosure may reduce the spread of bodily exudates throughout the articles. The reduced spreading of exudates may help to keep skin healthy by reducing the amount of skin exposed to the skin irritants within the exudates and/or by preventing additional skin irritants from being created by preventing the mixing of BM and urine, at least in proximity to the skin of the wearer.

Each example of this disclosure is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "stretch film laminate" refers herein to a laminate of an elastic film laminated to at least one outer layer of fibrous nonwoven web material. Desirably, the elastic film is air and vapor permeable and liquid impermeable and elastic in at least one and preferably two directions generally perpendicular to one another. More desirably, the elastic film is elastic in all directions of the X-Y plane of the material. In other embodiments, the elastic film can have cover layers, such as fibrous nonwoven web materials laminated to both sides of the elastic film so as so form a laminate with opposed exterior nonwoven layers, an intermediate layer of elastic film bonded to both of the exterior nonwoven layers. Further information can be found with reference to U.S. Pat. No. 7,803,244 to Siqueira et al. and U.S. Pat. No. 8,361,913 to Siqueira et al., each of which is incorporated herein in its entirety by reference.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Absorbent Article:

FIGS. 1-4 depict absorbent articles according to the present disclosure. One of the features of the present disclosure is the secondary liner sheet bonded to the body facing surface of the depicted absorbent articles and the BM containment flaps (also referred to herein as simply "containment flaps" or "flaps" or "BM flaps") of the absorbent articles. As mentioned, the secondary liner sheet may form a pocket, providing a barrier between a rear portion of the absorbent articles and a front portion of the articles. This barrier may help to prevent the spread of exudates and help to maintain healthy skin of the wearer.

Figure 1A:
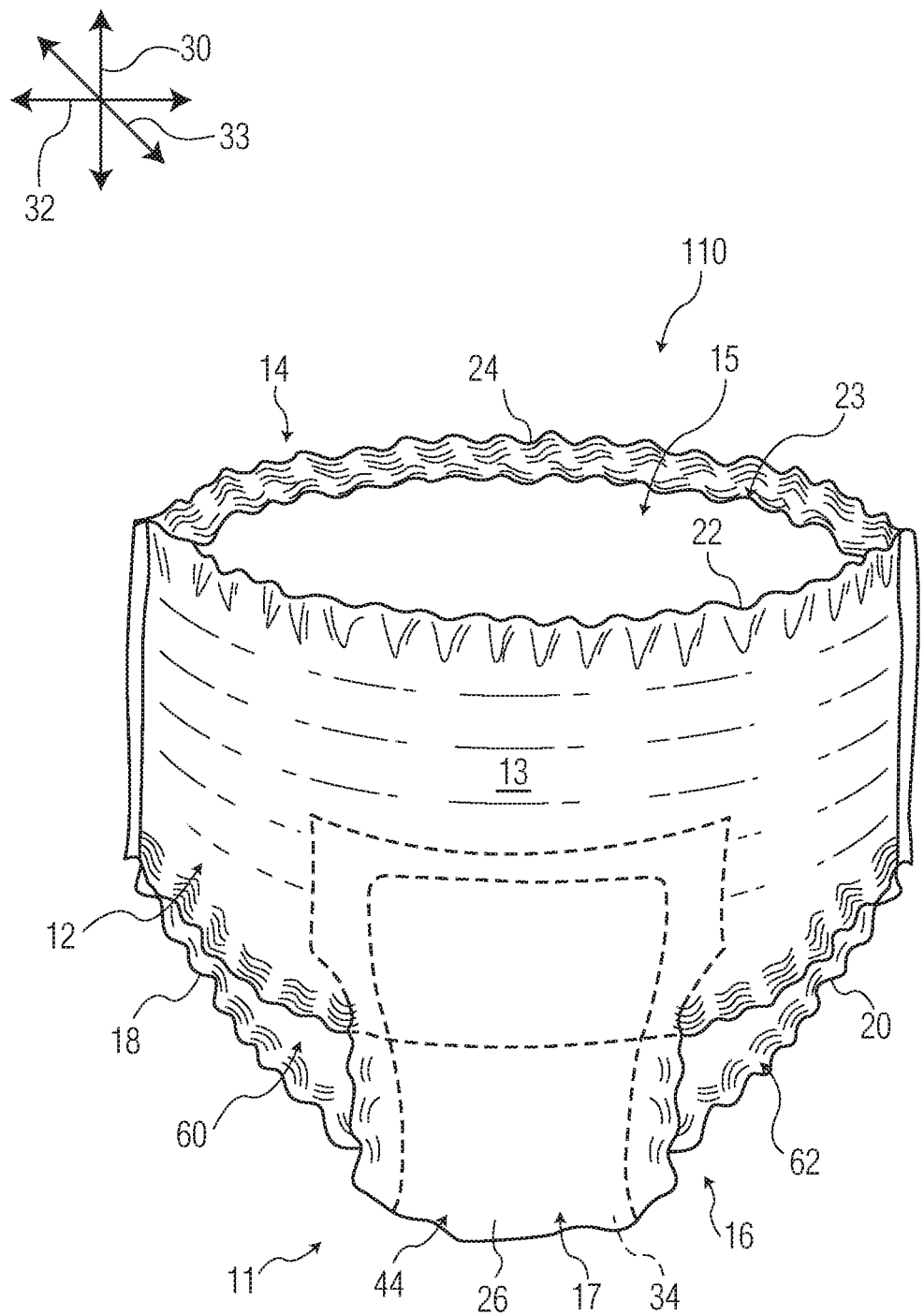
FIG. 1A perspective view of a different absorbent article according to aspects of the present disclosure.
Figure 2:
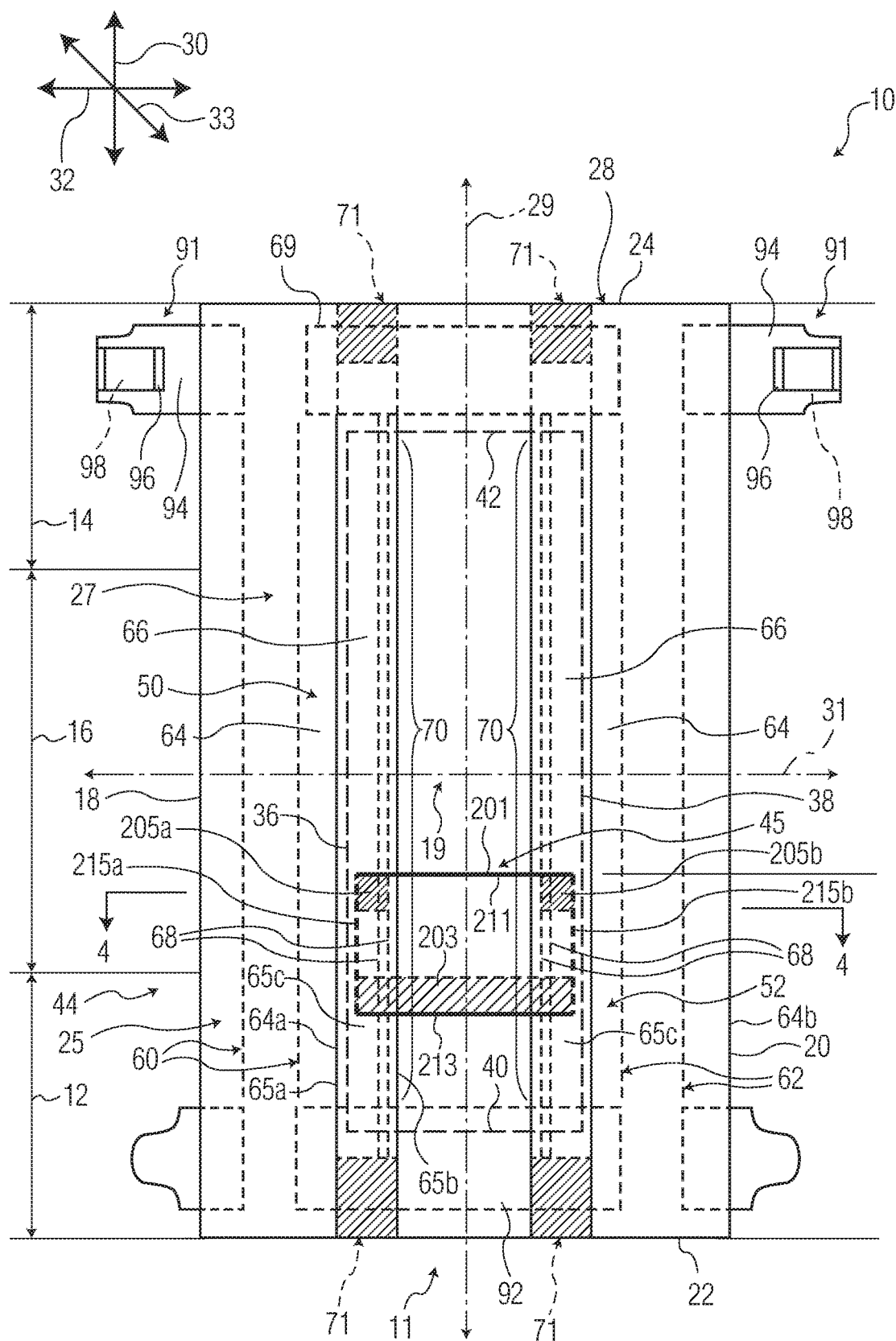
FIG. 2 is a top plan view of the absorbent article of FIG. 1 in a stretched, laid flat and unattached condition and including a connecting portion, according to aspects of the present disclosure.
Figure 2A:
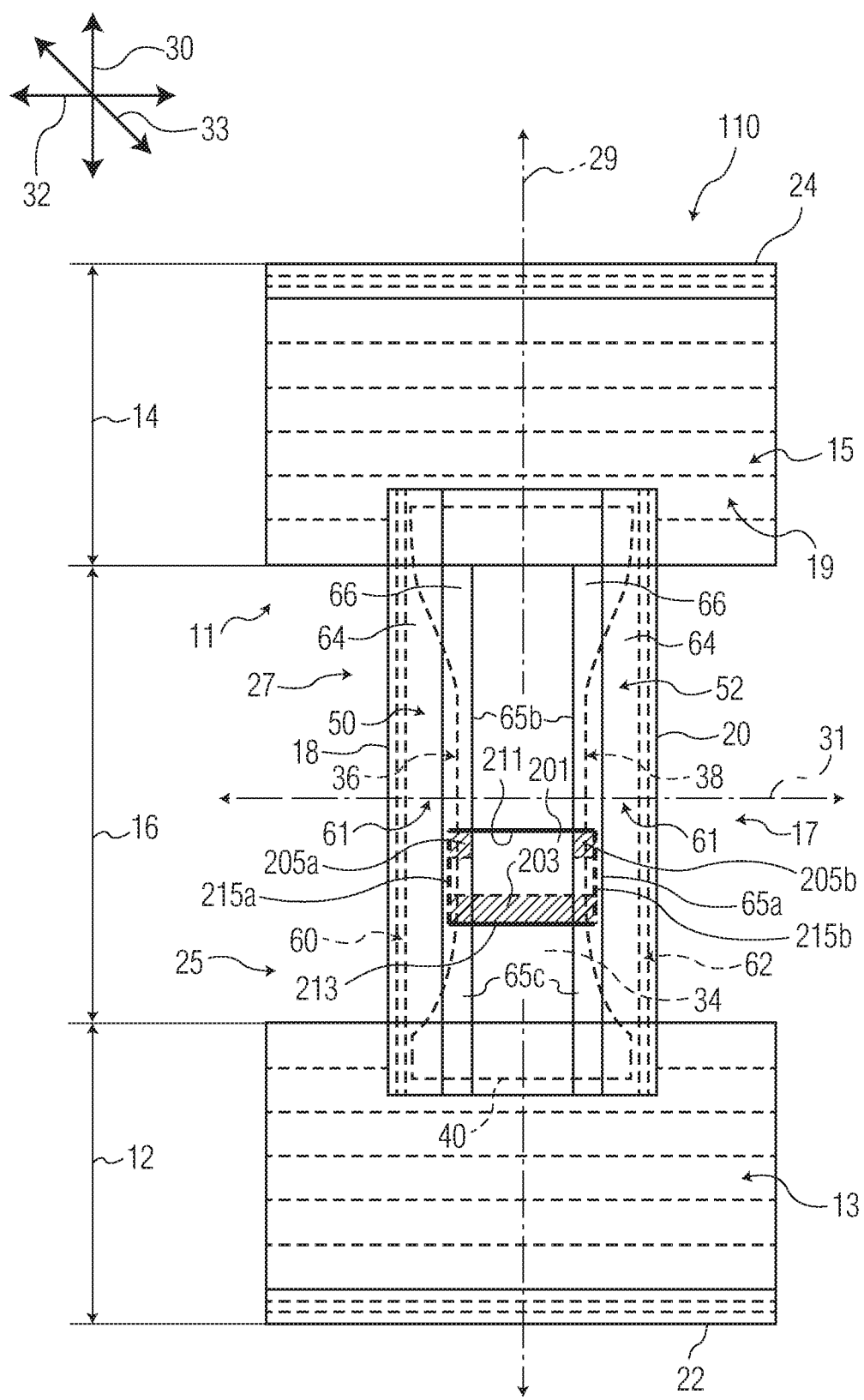
FIG. 2A is a top plan view of the absorbent article of FIG. 1A in a stretched, laid flat and unfastened condition and including a connecting portion, according to aspects of the present disclosure.

Referring to FIGS. 1 and 2, a non-limiting illustration of an absorbent article 10 for example, a diaper, is illustrated. Other embodiments of the absorbent article 10 can include, but are not limited to, training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. For example, the absorbent article 110 in FIGS. 1A and 2A provides an exemplary embodiment of an absorbent article 110 that can be manufactured in cross-direction manufacturing process.

The absorbent article 10 illustrated in FIGS. 1 and 2 can include a chassis 11. The absorbent article 10 can include a front waist region 12 and a rear waist region 14, and a crotch region 16 disposed between the front waist region 12 and the rear waist region 14 and interconnecting the front and rear waist regions, 12, 14, respectively. In the embodiment depicted in FIGS. 1A and 2A, a three-piece construction of an absorbent article 110 is depicted where the absorbent article 110 can have a chassis 11 including a front waist panel 13 defining the front waist region 12, a rear waist panel 15 defining the rear waist region 14, and an absorbent panel 17 defining the crotch region 16 of the absorbent article 110. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-direction without being a three-piece construction garment which is also sometimes referred to as a one-piece construction (not shown) as the front waist panel 13 and the rear waist panel 15 are integral with one another by way of commonly connected components forming the waist panel such as a body facing liner and/or a garment facing outer cover which can envelope the absorbent panel 17 or simply cover the garment facing side of the absorbent panel 17.

The absorbent article 10, 110 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10 illustrated in FIG. 2. In other embodiments, the longitudinal side edges 18, 20 can be curved between the front waist edge 22 and the rear waist edge 24. In the absorbent article 110 of FIGS. 1A and 2A, the longitudinal side edges 18, 20 can include portions of the front waist panel 13, the absorbent panel 17, and the rear waist panel 15.

The front waist region 12 can include the portion of the absorbent article 10, 110 that, when worn, is positioned at least in part on the front of the wearer while the rear waist region 14 can include the portion of the absorbent article 10, 110 that, when worn, is positioned at least in part on the back of the wearer. The crotch region 16 of the absorbent article 10, 110 can include the portion of the absorbent article 10, 110 that, when worn, is positioned between the legs of the wearer and can partially cover the lower torso of the wearer. Dimensionally, the front waist region 12 can be defined as the front one-third of the overall longitudinal dimension of the absorbent article 10 measuring from the front waist edge 22 to the rear waist edge 24. The rear waist region 14 can be defined as the rear one-third of the longitudinal dimension of the absorbent article 10 and the crotch region 16 is the middle one-third of the longitudinal dimension of the overall absorbent article 10. The waist edges, 22 and 24, of the absorbent article 10, 110 are configured to encircle the waist of the wearer and together define a central waist opening 23 (as labeled in FIG. 1 and FIG. 1A) for the waist of the wearer. Portions of the longitudinal side edges 18, 20 in the crotch region 16 can generally define leg openings for the legs of the wearer when the absorbent article 10, 110 is worn.

Figure 4:
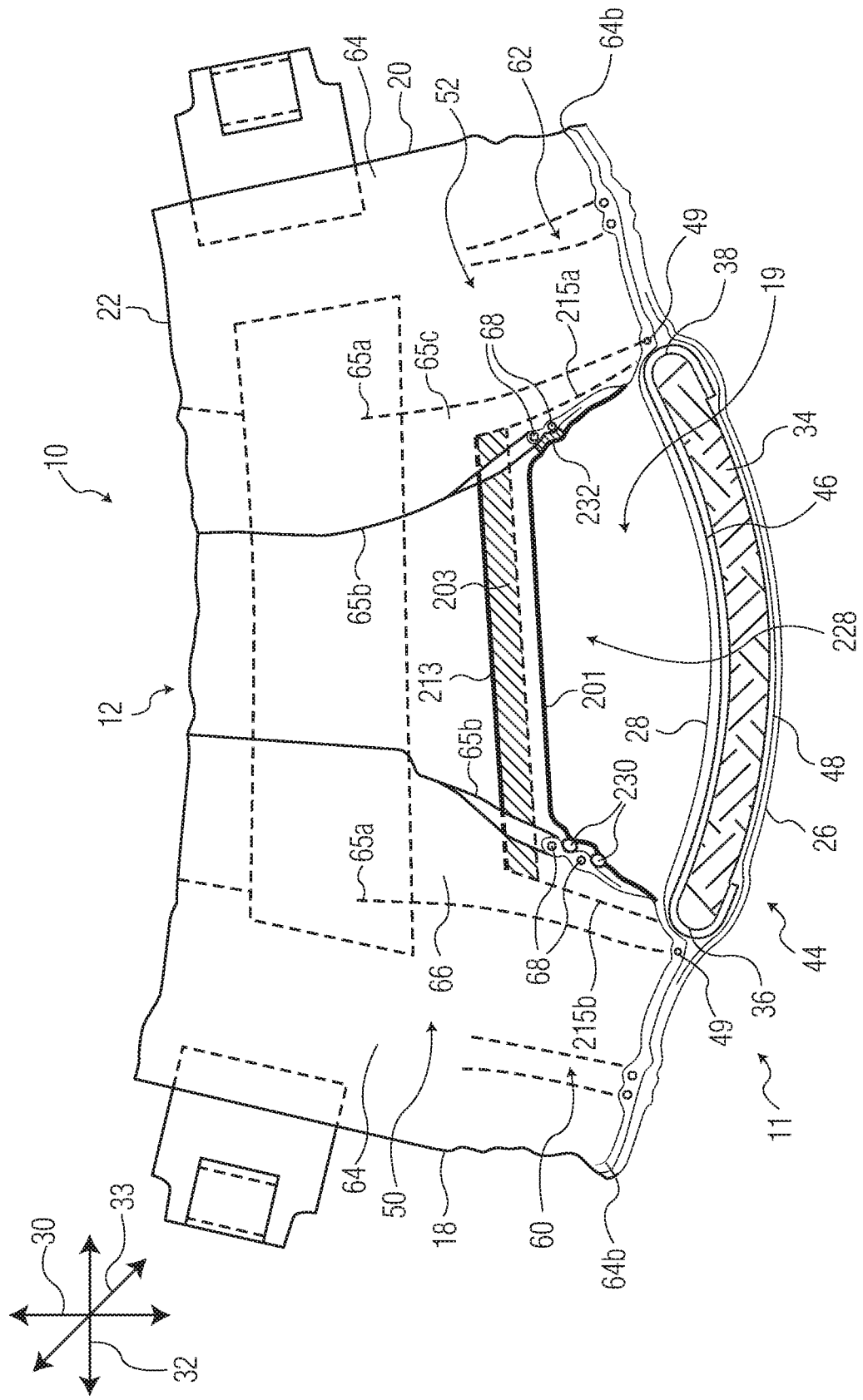
FIG. 4 is a cross-section of the absorbent article of FIG. 2 taken along line 3-3.

The absorbent article 10, 110 can include a garment facing outer cover 26 and a body facing liner 28. The outer cover 26 and the liner 28 can form a portion of the chassis 11 where the outer cover is disposed at the garment facing surface of the chassis (not shown; opposite body facing surface 19 of chassis 11) and the liner 28 is disposed at the body facing surface 19 of the chassis 11. In an embodiment, the liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIGS. 2 and 2A, the absorbent article 10, 110 can have a longitudinal axis 29 extending in the longitudinal direction 30, and a lateral axis 31 extending in the lateral direction 32. The lateral axis 31 is located midway between the front waist edge 22 and the rear waist edge 24, separating article 10 into front half section 25 and rear half section 27. As shown in FIG. 4, the absorbent article 10 also has a vertical or z-dimension extending in the vertical direction 33, which is perpendicular to both the longitudinal direction 30 and the lateral direction 32.

Figure 3:
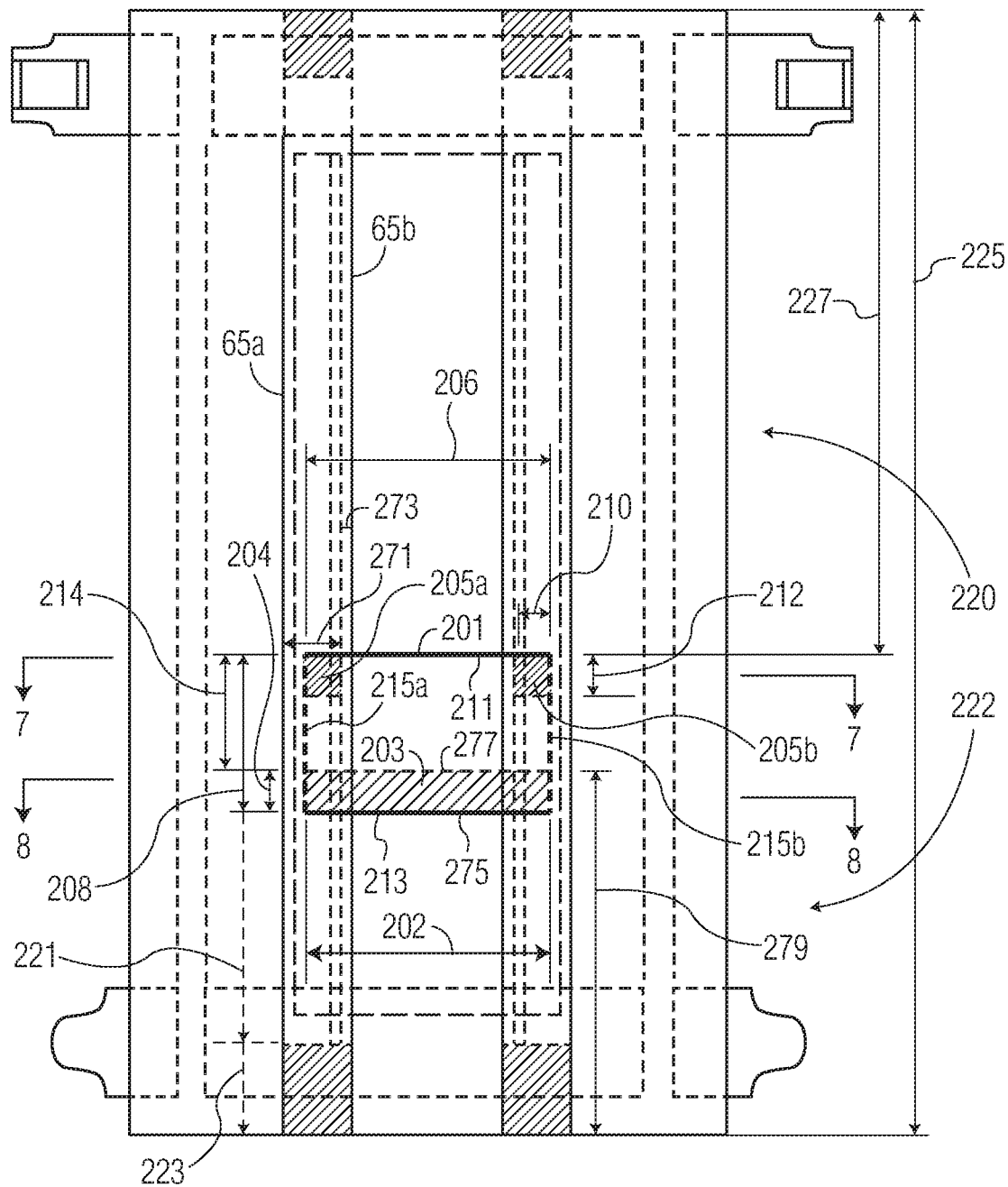
FIG. 3 is an alternative plan view of the absorbent article of FIG. 1A in a stretched, laid flat and unfastened condition and including a connecting portion, according to aspects of the present disclosure.

The chassis 11 can include an absorbent body 34. The absorbent body 34 can be disposed between the outer cover 26 and the liner 28. The absorbent body 34 can have longitudinal edges, 36 and 38, which, in some embodiments, can form portions of the longitudinal side edges, 18 and 20, respectively, of the absorbent article 10, 110. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 110. The liner 28, the outer cover 26, and the absorbent body 34 can form part of an absorbent assembly 44. In the absorbent article 110 of FIGS. 1A and 2A, the absorbent panel 17 can form the absorbent assembly 44. The absorbent assembly 44 can also include a fluid transfer layer 46 and a fluid acquisition layer (not shown) between the liner 28 and the fluid transfer layer 46 as is known in the art. The absorbent assembly 44 can also include a spacer layer 48 (as shown in FIG. 3) disposed between the absorbent body 34 and the outer cover 26.

The absorbent article 10, 110 can be configured to contain and/or absorb liquid, solid, and semi-solid body exudates discharged from the wearer. To this end, the absorbent article 10, 110 is fitted with a pair of containment flaps 50, 52 which are configured to provide a barrier to the lateral flow of body exudates. In some further embodiments, the absorbent article 10, 110 can optionally include a waistband, such as waistband 69 depicted in dashed lines in FIGS. 2 and 4 which cooperates with the containment flaps 50, 52 to form a pocket to further retain body exudates. See, for example, PCT/US15/23620, filed 31 Mar. 2015; PCT/US15/23596, filed 31 Mar. 2015; PCT/US15/23637, filed 31 Mar. 2015; PCT/US15/38271, filed 29 Jun. 2015; PCT/US15/47672, filed 31 Aug. 2015; and 62/212,051, filed 31 Aug. 2015 each of which is incorporated herein by reference in its entirety. In some embodiments, the waist containment member can be disposed in the rear waist region 14 of the absorbent article 10, 110.

The absorbent article 10, 110 can further include leg elastic members 60, 62 as are known to those skilled in the art. The leg elastic members 60, 62 can be attached to the outer cover 26 and/or the liner 28 along the opposite longitudinal side edges, 18 and 20, and positioned in the crotch region 16 of the absorbent article 10, 110. The leg elastic members 60, 62 can be parallel to the longitudinal axis 29 as shown in FIGS. 2 and 2A or can be curved as is known in the art. The leg elastic members 60, 62 can provide elasticized leg cuffs.

Additional details regarding each of the above described elements of the absorbent article 10, 110 described herein can be found below and with reference to the FIGS. 1-4. Details of the secondary liner sheet 201 are also described in detail below with respect to FIGS. 1-10.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 110. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the liner 28 can be constructed as described herein and it also may be apertured to enhance evaporation of urine in the event the inner layer is vapor permeable.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 110 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10, 110 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 110. The absorbent body 34 can have a length and width that can be less than or equal to the length and width of the absorbent article 10, 110.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material or in an alternate embodiment be comprised entirely of superabsorbent material.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 3. The absorbent body 34 can be bonded to the fluid transfer layer 46 and/or the spacer layer 48. Typically the absorbent body 34 will be completely enveloped by a core wrap material such as a tissue wrap or a nonwoven material such a meltblown web, a spunbond web or both, but this is not required in all embodiments.

Body Facing Liner:

The liner 28 of the absorbent article 10, 110 can overlay the absorbent body 34 and the outer cover 26 and can isolate the wearer's skin from liquid waste retained by the absorbent body 34. In various embodiments, a fluid transfer layer 46 can be positioned between the liner 28 and the absorbent body 34. In various embodiments, an acquisition layer (not shown) can be positioned between the liner 28 and the absorbent body 34 or a fluid transfer layer 46, if present. In various embodiments, the liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the liner 28. It is contemplated that the liner 28 may be narrower than the outer cover 26. However, in other embodiments, the liner 28 and the outer cover 26 may be of the same dimensions in width and length, for example, as depicted in the embodiments illustrated in FIG. 1. In other embodiments, the liner 28 can be of greater width than the outer cover 26. It is also contemplated that the liner 28 may not extend beyond the absorbent body 34 and/or may not be secured to the outer cover 26. In some embodiments, the liner 28 can wrap at least a portion of the absorbent body 34, including wrapping around both longitudinal edges 36, 38 of the absorbent body 34, and/or one or more of the end edges 40, 42. It is further contemplated that the liner 28 may be composed of more than one segment of material such as a central region of material which is different from one or both of the lateral regions of the liner 28 (not shown). The liner 28 can be of different shapes, including rectangular, hourglass, or any other shape. The liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the liner 28. The liner 28 can include a woven fabric, a non-woven fabric, a polymer film, a film-fabric laminate or the like, as well as combinations thereof. Examples of a non-woven fabric can include spunbond fabric, meltblown fabric, coform fabric, carded web, bonded-carded web, bicomponent spunbond fabric, spunlace, or the like, as well as combinations thereof. The liner 28 need not be a unitary layer structure, and thus, can include more than one layer of fabrics, films, and/or webs, as well as combinations thereof. For example, the liner 28 can include a support layer and a projection layer that can be hydroentangled. The projection layer can include hollow projections, such as those disclosed in U.S. Pat. No. 9,327,473 to Kirby et al.

For example, the liner 28 can be composed of a meltblown or spunbond web of polyolefin fibers. Alternatively, the liner 28 can be a bonded-carded web composed of natural and/or synthetic fibers. The liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire liner 28 or it can be selectively applied to particular sections of the liner 28.

In an embodiment, a liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a liner 28 can be a spunbond substrate with a basis weight from about 10 or 12 to about 15 or 20 gsm. In an embodiment, a liner 28 can be a 12 gsm spunbond-meltblown-spunbond substrate having 10% by weight of the meltblown content applied between the two spunbond layers.

Although the outer cover 26 and liner 28 can include elastomeric materials, it is contemplated that the outer cover 26 and the liner 28 can be composed of materials which are generally non-elastomeric. In an embodiment, the liner 28 can be stretchable, and more suitably elastic. In an embodiment, the liner 28 can be suitably stretchable and more suitably elastic in at least the lateral or circumferential direction of the absorbent article 10, 110. In other aspects, the liner 28 can be stretchable, and more suitably elastic, in both the lateral and the longitudinal directions 32, 30, respectively.

Containment Flaps:

In an embodiment, the absorbent article 10, 110 can include a pair of containment flaps 50, 52. Examples of containment flaps can be found in U.S. Pat. No. 9,259,362 granted 16 Feb. 2016 Robert L. Popp et al. and U.S. Pat. No. 9,168,181 granted 27 Oct. 2015 Robert L. Popp et al. each of which is incorporated herein by reference in its entirety.

The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 110 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art. In other embodiments, such as the absorbent article 110 in FIGS. 1A and 2A, the containment flaps 50, 52 can be disposed on the absorbent panel 17 in the crotch region 16.

In embodiments where the containment flaps 50, 52 are coupled to the chassis 11, the containment flaps 50, 52 can be attached to the liner 28 throughout a first attachment region 49, as shown in FIG. 4, or the containment flaps 50, 52 can be attached to the outer cover 26 throughout the first attachment region 49, for instance in at least some embodiments where the liner 28 does not extend the full lateral width of the outer cover 26. Of course, the containment flaps 50, 52 can be attached to other components of the chassis 11. Exemplary attachment means for attaching the containment flaps 50, 52 to the liner 28 and/or the outer cover 26 include, but are not necessarily limited to, adhesives, pressure bonds, heat bonds, and ultrasonic bonds. The containment flaps 50, 52 can be constructed of a fibrous material which can be similar to the material forming the liner 28, including, but not limited to a spunbond-meltblown-spunbond ("SMS") material. Other conventional materials, including, but not limited to, polymer films, can also be employed. In addition, laminates of materials including multiple layers of film and/or nonwovens can be used to form the containment flap material.

The containment flaps 50, 52 in an embodiment such as is shown in FIGS. 1-4 can each include a base portion 64 and a projection portion 66. The base portion 64 and the projection portion 66 can be formed from the same materials or from different materials. In an embodiment, the containment flaps 50, 52 can comprise only the projection portion 66 with the projection portion 66 defining the entire containment flap 50, 52. In such situations, the base portion 64 may be eliminated or it may be formed from one of the other components such as an extension of the liner 28, the outer cover 26 or from a separate and distinct piece of material (not shown).

The base portion 64 can be bonded to the chassis 11, for example, to the liner 28 or the outer cover 26 or another component of the chassis 11. The base portion 64 can include an interior end 64a and an exterior end 64b. The projection portion 66 can be separated from the base portion 64 at the interior end 64a of the base portion 64. As used in this context, the projection portion 66 is separated from the base portion 64 at the interior end 64a of the base portion 64 in that the interior end 64a of the base portion 64 defines a transition between the projection portion 66 and the base portion 64. The interior end 64a of the base portion 64 can be located near and/or utilize all or a portion of the first attachment region 49 or a separate attachment region 49 or other attachment means. In some embodiments, the exterior ends 64b of the base portion 64 of the containment flaps 50, 52 can laterally extend to the respective longitudinal side edges 18, 20 of the absorbent article 10. In other embodiments, the exterior ends 64b of the base portion 64 can end laterally inward of the respective longitudinal side edges 18, 20 of the absorbent article 10, 110. The containment flaps 50, 52 also each include a projection portion 66 that is configured to extend away from the body facing surface 19 of the chassis 11 at least in the crotch region 16 when the absorbent article 10 is in a relaxed configuration, as illustrated in FIG. 4. The containment flaps 50, 52 can include a tack-down region 71 in either or both of the front waist region 12 and the rear waist region 14 where the projection portion 66 is coupled to the body facing surface 19 of the chassis 11, as can be seen in FIG. 2.

In a more simplified version, the base portion 64 of the containment flaps 50, 52 can be eliminated (not shown) or can be made from a separate piece of material such that the projection portion 66 forms the entire containment flap 50, 52. In this case, the containment flaps 50, 52 can be regarded as having a proximal edge 65a and a distal edge 65b joined by a medial section 65c. See in particular, FIGS. 2, 3, and 4. The proximal edge 65a can be attached to the chassis 11 including direct or indirect attachment to any of the components including the liner 28, the outer cover 26 or any of the other components of the absorbent article 10. Thus, the first attachment region 49 can be used to attach the proximal edge 65a to the chassis 11 and this first attachment region 49 can be the same as or separate from the attachment region used to attach the interior end 64a of the base portion 64 to the chassis 11.

It is contemplated that the containment flaps 50, 52 can be of various configurations and shapes, and can be constructed by various methods. For example, the containment flaps 50, 52 of FIG. 2 depict a vertical containment flap 50, 52 with a tack-down region 71 in both the front and rear waist regions 12, 14 where the projection portion 66 of each containment flap 50, 52 is tacked down to the liner 28 towards or away from the longitudinal axis 29 of the absorbent article 10. However, the containment flaps 50, 52 can include a tack-down region 71 where the projection portion 66 of each of the containment flaps 50, 52 is folded back upon itself and coupled to itself and the liner 28 in a "C-shape" configuration, as described in U.S. Pat. No. 5,895,382 to Robert L. Popp et al. As yet another alternative, it is contemplated that the containment flaps 50, 52 can be constructed in a "T-shape" configuration, such as described in U.S. Pat. No. 9,259,362 by Robert L. Popp et al. Such a configuration can also include a tack-down region 71 in either or both of the front and rear waist regions 12, 14, respectively. Of course, other configurations of containment flaps 50, 52 can be used in the absorbent article 10, 110 and still remain within the scope of this disclosure.

The containment flaps 50, 52 can include one or more flap elastic members 68, such as the two flap elastic strands depicted in FIGS. 2-4. Of course, while two elastic members 68 are shown in each containment flap 50, 52, it is contemplated that the containment flaps 50, 52 can be configured with one or three or more elastic members 68. As shown in the Figures, the elastic members 68 are located adjacent the flap distal edges 65b but they can also be located in any other portion of the containment flaps including adjacent the flap proximal portion 65a and the flap medial portion 65c.

Suitable elastic materials for the flap elastic members 68 can include, but are not limited to, spandex elastomeric strands, sheets, strands, or ribbons of natural or synthetic rubber, thermoplastic elastomeric materials, or heat activated elastomeric materials. The elastic members 68 can be any elastomeric material capable of being elongated at least about 50 percent, desirably about 350 percent, and capable of recovering to within at least about 250 percent, and desirably about 150 percent of its original length after being elongated about 300 percent. The elastic members 68 can be a spandex elastomeric strand(s) such as, for example, a LYCRA thread commercially available from E. I. DuPont de Nemours and Co. Alternatively, the elastic members 68 can be composed of a thermoplastic elastomer or a natural or a synthetic rubber commercially available from J.P.S. Elastomerics Corp. Alternatively, the elastic members 68 can also be composed of a heat activated elastic material such as PEBAX, commercially available from Atochem, Inc., which can be activated with heat treatment after the elastic members 68d are secured to the containment flaps 50, 52.

Alternatively or additionally, the containment flaps 50, 52 can be composed of a material exhibiting elastic properties itself thereby eliminating the need for the use of separate flap elastic members 68. In an alternate embodiment, the containment flaps 50, 52, and in particular the projection portions 66, can be formed from an elastic material or laminate such as a stretch film laminate as described herein which optionally can be supplemented with flap elastics adjacent the distal edges 65b, alternately adjacent the proximal edges 65a, alternately adjacent the medial section 65c/41 or a combination of any or all of the foregoing regions of the projection portions 66 forming the containment flaps 50, 52. Example suitable materials that may be used as containment flaps 50, 52 include vertical film laminate materials, stretch film laminate materials, or elastic laminate structures. One specific example material is the elastic film laminate material called SABBEEL herein, which is described in U.S. Pat. No. 8,287,677, titled "Printable Elastic Composite" and is expressly incorporated herein in its entirety. Additionally, it should be understood that these are only example materials. More generally, any material having at least some of the below described properties are contemplated by this disclosure for use as containment flaps 50, 52.

The flap elastic members 68, as illustrated in FIGS. 2-4, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 19 of the chassis 11 in a generally upright orientation of the containment flaps 50, 52, especially in the crotch region 16 of the absorbent article 10, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. The elastic members 68 can be coated with adhesive while elongated to a specified length prior to attaching the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2, which will gather upon relaxation of the absorbent article 10. The active flap elastic region 70 of containment flaps 50, 52 can be of a longitudinal length that is less than the length of the absorbent article 10, 110. In this exemplary method of bonding the elastic members 68 to the containment flaps 50, 52, the portion of the elastic members 68 not coated with adhesive will retract after the elastic members 68 and the absorbent article 10 are cut in manufacturing to form an individual absorbent article 10. As noted above, the relaxing of the elastic members 68 in the active flap elastic region 70 when the absorbent article 10, 110 is in a relaxed condition can cause each containment flap 50, 52 to gather and cause the projection portion 66 of each containment flap 50, 52 to extend away from the body facing surface 19 of the chassis 11, as depicted in FIG. 4.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10, 110. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the liner 28 as depicted in FIGS. 2-4, between the base portion 64 of each containment flap 50, 52 and the outer cover 26, or between the liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can also be omitted from the absorbent article 10, 110 without departing from the scope of this disclosure.

Fastening System:

In an embodiment, the absorbent article 10, can include a fastening system. The fastening system can include one or more back fasteners 91 and one or more front fasteners 92. The embodiments being shown in FIGS. 1 and 2 depict embodiments with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

Turning to FIGS. 2 and 2A, exemplary articles 10, 110 of the present disclosure may further comprise a secondary liner sheet 201. FIG. 3 is another perspective of the article 10 including the secondary liner sheet 201 where the secondary liner sheet 201 may be seen more clearly. As can be seen in FIGS. 2 and 3, the secondary liner sheet 201 may have a rear sheet edge 211, a front sheet edge 213, and laterally spaced side edges 215a, 215b. The secondary liner sheet 201 additionally has a lateral sheet width 206 and a longitudinal sheet length 208.

In at least some embodiments, the laterally spaced side edges 215a, 215b may be spaced laterally inward of the proximal edges 65a of containment flaps 50, 52. That is, the lateral sheet width 206 may be chosen to be anywhere between about 1 mm to about 30 mm less than distance between the attachment points of containment flap 50 and containment flap 52 to the chassis 11 (e.g. attachment regions 49), or any width between about 1 mm and about 30 mm less than the distance between the attachment regions 49 where the proximal edges 65a of the containment flaps 50, 52 at attached to the chassis 11. In other embodiments, the lateral sheet width 206 may be chosen to be anywhere between about 1 mm to about 25 mm, about 5 mm to about 25 mm, about 5 mm to about 20 mm, or about 5 mm to about 10 mm less than distance between the attachment regions 49. In still other embodiments, the laterally spaced side edges 21a, 21b may extend all the way to the attachment regions 49, while in other embodiments the laterally spaced side edges 21a, 21b may be located outboard of the proximal edges 65a.

In the longitudinal 30 dimension, the secondary liner sheet 201 may also vary in different embodiments. However, in at least some embodiments, the longitudinal sheet length 208 may be between about 60 mm to about 300 mm. In other embodiments, the longitudinal sheet length 208 may be between about 60 mm and about 150 mm. In still further embodiments, the longitudinal sheet length 208 may be about 60 mm, about 65 mm, about 70 mm, about 75 mm, about 80 mm, about 85 mm, about 90 mm, about 95 mm, about 100 mm, or any other suitable value. The lateral sheet width 206 may also vary in different embodiments, but may generally range between about 50 mm and about 200 mm. In some embodiments, the lateral sheet width 206 is less than the longitudinal sheet length 208.

The secondary liner sheet 201 may additionally be bonded to the article 10 at least by a liner attachment bond 203 and flap attachment bonds 205a, 205b. The liner attachment bond 203 may attach the secondary liner sheet 201, proximate the front sheet edge 213, to the liner 28. The liner attachment bond 203 has a lateral bond width 202 (as seen in FIG. 3) and a longitudinal bond length 204. In some embodiments, the lateral bond width 202 may be equal to the lateral sheet width 206. That is, the liner attachment bond 203 may extend all the way between the laterally spaced side edges 21a, 21b. However, in other embodiments, lateral bond width 202 may be less than lateral sheet width 206. For instance, in some embodiments, the lateral bond width 202 may be between about 75% and about 95% of the lateral sheet width 206. Generally, the lateral bond width 202 may be sufficient for a first end of the liner attachment bond 203 to be disposed under containment flap 50 while the second end of the liner attachment bond 203 is disposed under containment flap 52.

In different embodiments, the longitudinal bond length 204 may be between about 5 mm and about 40 mm long. In other embodiments, the longitudinal bond length 204 may be chosen to be a percentage of the longitudinal sheet length 208. For instance, the longitudinal bond length 204 may be between about 5% and about 50% of the longitudinal sheet length 208. One advantage of a larger longitudinal bond length 204 is that the liner attachment bond 203 maintains close contact between the secondary liner sheet 201 and the liner 28, and in embodiments where the secondary liner sheet 201 is hydrophilic, such a close attachment allows for better transfer of liquid from the secondary liner sheet 201 to the liner 28 and further into the absorbent article 10.

The liner attachment bond 203 may further be defined by a front bond edge 275 and a rear bond edge 277. In some embodiments, it may be advantageous to ensure that the liner attachment bond 203 is located at a particular position within the article 10. For instance, it may be beneficial for the liner attachment bond 203 to be located within the article 10 where urine insults tend to occur. As mentioned, the liner attachment bond 203 ensures a close relation between the secondary liner sheet 201 and the body facing liner 28 helping to hasten fluid transfer from the secondary liner sheet 201 to the liner 28, and into the interior of the article 10, such as into the absorbent body 34.

Common insult locations for both boys and girls have been found through testing. For girls, it has been found that insults commonly happen in an area of absorbent articles, such as article 10, that is located away from the front waist edge 22 a distance that is about 36% of the total length 225 of the article 10. Accordingly, in some embodiments the rear bond edge 277 of the liner attachment bond 203 may be spaced away from the front waist edge 22 of the article 10 a distance that is at least about 40% of the total length 225 of the article 10 to ensure that the liner attachment bond 203 covers a region of the article 10 where urine insults commonly occur for girls. In further embodiments, the rear bond edge 277 of the liner attachment bond 203 may be spaced away from the front waist edge 22 of the article 10 a distance that is at least about 35% of the total length 225 of the article 10. For boys, it has been found that insults commonly happen in an area of absorbent articles, such as article 10, that is located away from the front waist edge 22 a distance that is about 28% of the total length 225 of the article 10. Accordingly, in some embodiments the rear bond edge 277 of the liner attachment bond 203 may be spaced away from the front waist edge 22 of the article 10 a distance that is at least about 30% of the total length 225 of the article 10 to ensure that the liner attachment bond 203 covers a region of the article 10 where urine insults commonly occur for boys. In general, the rear bond edge 277 of the liner attachment bond 203 may be spaced away from the front waist edge 22 of the article 10 a distance that is between about 25% and about 40% of the total length 225 of the article 10.

In any of the above embodiments, it may be beneficial for the front bond edge 275 to be located within particular regions of the article 10 in order to ensure that the liner attachment bond 203 spans a desired region of the article 10. For instance, it may be beneficial for the front bond edge 275 of the liner attachment bond 203 to be spaced away from the front waist edge 22 of the article 10 a distance that is less than or equal to about 30% of the total length 225 of the article 10. In further embodiments, the front bond edge 275 of the liner attachment bond 203 may be spaced away from the front waist edge 22 of the article 10 a distance that is less than or equal to about 25% of the total length 225 of the article 10. In general, the front bond edge 275 of the liner attachment bond 203 may be spaced away from the front waist edge 22 of the article 10 a distance that is between about 20% and about 35% of the total length 225 of the article 10. Accordingly, in different embodiments, the liner attachment bond 203 may have a longitudinal bond length 204 that is between about 0% (e.g. has a negligible bond length 204 of 1% or less of the total length 225 of the article 10) and about 20% of the total length 225 of the article 10.

In further embodiments, only one of the front bond edge 275 or the rear bond edge 277 may be located within the above described regions, e.g. located a distance away from the front waist edge 22 a distance of between about 20% and about 40% of the total length 225 of the article 10. In such embodiments, the liner attachment bond 203 may have a longitudinal bond length 204 that is between about 1% and about 20% of the total length 225 of the article 10, or between about 1% and about 15% of the total length 225 of the article 10, or between about 5% and about 15% of the total length 225 of the article 10. Lengths in these described ranges may ensure coverage of the liner attachment bond 203 within desired regions of the article, such as common regions where urine insults occur.

The secondary liner sheet 201 may also have a rear un-bonded length 214, which is the distance between the rear bond edge 277 and the rear sheet edge 11. This rear un-bonded length 214 essentially defines a 'depth' of the pocket 228 (as shown in FIG. 4). The rear un-bonded length 214 may generally be between about 20 mm and about 15 mm, or between about 20 mm and about 80 mm, or between about 40 mm and 80 mm, regardless of the longitudinal length of the secondary liner sheet 201. In other embodiments, the rear un-bonded length 214 may be between about 4% and about 30% of the longitudinal length 225 of the article 10 as shown in FIG. 3, or between about 10% and about 25% in other embodiments. In at least some further embodiments, the rear un-bonded length 214 may be chosen to be greater than or equal to the distance between proximal edge 65a and distal edge 65b of containment flaps 50, 52.

In at least some embodiments, the secondary liner sheet 201 may have one or more other features. For instance, the secondary liner sheet 201 may be opaque in order to hide BM exudates that have been captured under the un-bonded portion of the secondary liner sheet 201. For instance, the secondary liner sheet 201 may have a basis weight of between about 25 gsm and about 35 gsm, which provides the secondary liner sheet 201 with enough density to hide exudates disposed under the secondary liner sheet 201. In additional or alternative embodiments to the embodiments where the secondary liner sheet 201 is opaque, the secondary liner sheet 201 may have a fiber content of between about 30% and about 100% poly-propylene (pp) fibers, or between about 50% and 100% pp fibers. In at least some of these embodiments where the secondary liner sheet 201 comprises between about 30% and about 100% pp fibers, the secondary liner sheet 201 may be attached to the containment flaps 50, 52 through only pressure bonds. Additionally or alternatively to any of the above optional features, the secondary liner sheet 201 may be more permeable and/or hydrophilic than the liner 28.

The flap attachment bonds 205a, 205b may attach the secondary liner sheet 201 to both containment flap 50 and containment flap 52. Each of the flap attachment bonds 205a, 205b may have a lateral bond width 210 and a longitudinal bond length 212. In some embodiments, the flap attachment bonds 205a, 205b may be square such that the lateral bond width 210 equals the longitudinal bond length 212. However, in other embodiments, the lateral bond width 210 may be less than the longitudinal bond length 212. For instance, in some embodiments, the lateral bond width 210 may be between about 25% to about 75% of the value of the longitudinal bond length 212. For example, if the longitudinal bond length 212 is 30 mm, then the lateral bond width 210 may be between about 7.5 mm and about 22.5 mm. In at least some embodiments, the lateral bond width 210 may be 15 mm while the longitudinal bond length 212 is 30 mm. In some further embodiments, the value of the longitudinal bond length 212 may be chosen as function of the sheet longitudinal length 208. For instance, the longitudinal bond length 212 may be between about 25% and about 45% of the longitudinal sheet length 208.

In general, the longitudinal bond length 212 may be determined as the length of an edge of the flap attachment bonds 205a, 205b most proximate to the distal edges 65b of the containment flaps 50, 52. For instance, where the flap attachment bonds 205a, 205b are square and have edges parallel to the distal edges 65b of the containment flaps 50, 52, the longitudinal bond length 212 is simply the length of such edges. Where the flap attachment bonds 205a, 205b have an angled edge most proximate the distal edges 65b of the containment flaps 50, 52, the longitudinal bond length 212 may be the length of the angled edges in the longitudinal direction 30 of the article 10. Where the flap attachment bonds 205a, 205b are circular or oval-shaped, the longitudinal bond length 212 may simply be the longest extent of the flap attachment bonds 205a, 205b in the longitudinal direction 30. Where the flap attachment bonds 205a, 205b comprise individual point bonds, such individual point bonds may be considered together to form the flap attachment bonds 205a, 205b. In such embodiments, the flap attachment bonds 205a, 205b may have a shape produced by connecting the individual point bonds to form a perimeter around the individual point bonds.

In still further embodiments, it may be beneficial for the longitudinal bond length 212 to be relatively long, such as for example greater than about 8% of the total length 225 of the absorbent article 10. The longitudinal bond length 212 relates to how much of the secondary liner sheet 201 is lifted above the liner 28. Having a relatively greater amount of the secondary liner sheet 201 lifted above the liner 28 may allow for better utilization of the pocket 228 which is formed by the secondary liner sheet 201. However, it is possible for the longitudinal bond length 212 to become too great such that the lifted portion of the secondary liner sheet 201 interferes with the fit or function of the article 10. For instance, if the lifted portion of the secondary liner sheet 201 is disposed proximate portions of the article 10 where urine insults generally occur, the lifted portion may interfere with the transfer of the insulted liquid into the article 10. Accordingly, the longitudinal bond length 212 may generally be less than or equal to about 16% of the total length 225 of the absorbent article 10 in order to the lifted portion does not encroach on potential urine insult locations of the article 10. In other embodiments, the longitudinal bond length 212 may be between about 8% and about 14% of the total length 225 of the absorbent article 10, or between about 10% and about 14% of the total length 225 of the absorbent article 10, between about 10% and about 12% of the total length 225 of the absorbent article 10, or any other suitable value.

In general, the liner attachment bond 203 and the flap attachment bonds 205a, 205b may attach the liner 28 to the secondary liner sheet 201 and the secondary liner sheet 201 to the containment flaps 50, 52, respectively, by adhesive bonding, ultrasonic bonding, thermal bonding, pressure bonding, or other conventional bonding. Further, in at least some embodiments the liner attachment bond 203 and the flap attachment bonds 205a, 205b may comprise different types of bonds. For instance, the liner attachment bond 203 may comprise and adhesive bond while the flap attachment bonds 205a, 205b may comprise pressure bonds. Additional features of the liner attachment bond 203 and the flap attachment bonds 205a, 205b, for instance their location in relation to one or more components of the article 10, is described in more detail below with respect to FIGS. 4, 7, and 8.

As described above, the secondary liner sheet 201 is attached to the liner 28 proximate the front sheet edge 213 and to the containment flaps proximate the rear sheet edge 211. When the article 10 is disposed in a relaxed or wear configuration, the flap elastics 68 may contract and cause the proximal edges 65a of the containment flaps 50, 52 to lift away from the liner 28. This action also lifts the rear sheet edge 211 of the secondary liner sheet 201 away from the liner 28, forming a pocket facing the rear waist region 14. Accordingly, the secondary liner sheet 201 may form a barrier between a rear zone and a front zone of the article 10. In some embodiments, the rear zone and the front zone may be differentiated into a rear BM management zone 220 and a front urine management zone 222. However, it should be understood this is not the case in all embodiments. In at least some embodiments, the front and rear zones may be substantially similar except for the secondary liner sheet 201 being located within the front zone.

Where the front and rear zones are differentiated, the rear BM management zone 220 may be configured to better handle BM than the front urine management zone 222. In some embodiments, the rear BM management zone 220 may comprise a plurality of apertures (not shown) that better allow for intake of BM exudates. In other embodiments, liner 28 within the rear BM management zone 220 may have a first set of properties more suited to handling BM exudates, while the liner 28 within the front urine management zone 222 may have a second set of properties less suited to handling of BM exudates. Instead of the liner 28 being differentiated between each of the zones 220, 222, each of the rear BM management zone 220 and the front urine management zone 222 may include different topical surge materials on top of the liner 28 that provide the differentiated properties for BM management and urine management.

Accordingly, the front urine management zone 222 may be more suited to handling urine than the rear BM management zone 220. For instance, the combined topical materials of the front urine management zone 222 (which comprise a liner and optional topical surge) may have a greater basis weight than the combined topical materials of the rear BM management zone 220 in order to more effectively absorb and distribute urine within the front urine management zone 222. Additionally, or alternatively, the urine management zone 222 may be more hydrophilic than the rear BM management zone 220, as the urine management zone 222 may be more suited for quick intake of liquid exudates.

In still further embodiments, the secondary liner sheet 201 may be the material that provides the differentiated absorption and distribution properties of the front urine management zone 222 with respect to the rear BM management zone 220. For example, the liner 28 may have the same properties throughout the rear BM management zone 220 and the front urine management zone 222. The secondary liner sheet 201 may then overlay the liner 28 within a least a portion of the front urine management zone 222 in order to create a region with enhanced urine management properties. For instance, the secondary liner sheet 201 may provide the front urine management zone 222 with increased basis weight in relation to the rear BM management zone 220, which may provide better uptake and distribution (e.g. faster uptake and quicker distribution) of a urine insult within the front urine management zone 222 than if a urine insult happened within the rear BM management zone 220. More specifics about the properties of the secondary liner sheet 201 are described below with respect to FIG. 4.

Although depicted in FIG. 2 as having a longitudinal length 208 extending only through a portion of the crotch region 16 and/or the front waist region 12, in other embodiments, the secondary liner sheet 201 may have a longitudinal length 221 or 223. In the example where the secondary liner sheet 201 has a longitudinal length 221, the secondary liner sheet 201 may extend from the rear sheet edge 211 all the way to the tack down region 71 within the front waist region 12. In embodiments where the secondary liner sheet 201 has a longitudinal length 223, the secondary liner sheet 201 may extend all the way to the front waist edge 22. Of course, in other embodiments, the secondary liner sheet 201 may have a longitudinal length such that the front sheet edge 213 is disposed anywhere within the front waist region. In such examples where the secondary liner sheet 201 has a longitudinal length 221 or 223, or where the front sheet edge 213 of the secondary liner sheet 201 is located closer to the front waist edge 22 than depicted in FIG. 2, the liner attachment bond 203 may still be located in the same spot relative to the rear sheet edge 211 of the secondary liner sheet 201. That is, the liner attachment bond 203 may be located within a particular region of the article 10 without respect to how long or short the secondary liner sheet 201 is. In such embodiments, additional bond regions (not shown) may bond the secondary liner sheet 201 to other portions of the liner 28 in order to securely attach the secondary liner sheet 201 to the liner 28. In such embodiments, the liner attachment bond 203 is the bond that helps to the form the pocket facing the rear waist region 14. In still further embodiments, the longitudinal bond length 204 may extend the whole length of the secondary liner sheet 201 regardless of whether the secondary liner sheet 201 has a length 208, 221, 223, or other length. Further description of the liner attachment bond 203 and its relative location within the article 10 is discussed in more detail below.

One feature of the secondary liner sheet 201, and the pocket that it forms, is that the secondary liner sheet 201 helps prevent the spread of BM insulted in the rear zone 220—and it particularly helps prevent the spread the insulted BM forward of the liner attachment bond 203. In this manner, the secondary liner sheet 201 may help to prevent irritants within the BM exudates from reaching sensitive skin areas of a wearer located within the front waist region of the article 10 when worn. One important factor affecting this function of the secondary liner sheet 201 is the location of the secondary liner sheet 201 within the article 10.

The article 10 may have an overall article longitudinal length 225. In at least some embodiments, the article longitudinal length 225 may be between about 300 mm and about 600 mm. In other embodiments, the article longitudinal length 225 may be between about 400 mm and about 500 mm. In still other embodiments, the article longitudinal length 225 may be about 445 mm or about 476 mm. In different embodiments, the rear edge 211 of the secondary liner sheet 201 may be located at different locations in relation to the rear edge 211 of the secondary liner sheet 201. Additionally, it was hypothesized that different locations of the rear edge 211 of the secondary liner sheet 201 in relation to the rear waist edge 24 would affect the efficacy of the articles of the present invention in terms of preventing the spread of BM.

In order to determine the most effective location of the rear edge 211 of the secondary liner sheet 201 in relation to the rear waist edge 24 of the article 10, a test was performed with the rear edge 211 of the secondary liner sheet 201 at different locations with respect to the rear waist edge 24 of the article 10. Accordingly, a number of test articles were produced that are consistent with the examples described with respect to article 10, except that the distance of the rear edge 211 of the secondary liner sheet 201 in relation to the rear waist edge 24 of the article 10 varied between the test articles. All of the test articles were produced to be 445 mm in overall length. More specifically, four (4) test articles were each produced without the secondary liner sheet 201 as control samples. Additionally, four (4) test articles each were produced with the rear edge of the secondary liner sheet 201 located 230 mm from the rear waist edge 24 of the article 10, 242 mm from the rear waist edge 24 of the article 10, and 255 mm from the rear waist edge 24 of the article 10. In the data shown below (Tables 1-3), the test articles labeled code K comprise the control group with no secondary liner sheet, the test articles labeled code G comprise articles with the rear edge of the secondary liner sheet located 242 mm from the rear waist edge of the articles, the test articles labeled code L comprise articles with the rear edge of the secondary liner sheet located 230 mm from the rear waist edge of the articles, and the test articles labeled code J comprise articles with the rear edge of the secondary liner sheet located 255 from the rear waist edge of the articles.

Each of the test articles were tested according to a Simulation BM Insult Test Method. As part of the Simulation BM Insult Test Method, each of the samples was placed on a mannequin, and the mannequin was maneuvered to perform a walk-sit-crawl-stand sequence in order to pre-condition each test article.

Next, 140 ml of BM simulant was excreted onto the test articles through a tube within the mannequin. The BM simulant consisted of 453 g of pumpkin puree, 453 g of refried beans, 1 snack-pack size cup of chocolate pudding, 100 g Nesquik, 100 g flour, and 1 egg white all blended together, for example in a standard kitchen mixer.

After the BM simulant was excreted onto the test articles, each of the test articles was then subjected to the same walk-sit-crawl-stand maneuvers used to pre-condition the test articles. Finally, the test articles were removed from the mannequins and three separate measurements were taken to determine overall performance of each of the test articles.

A first measurement was taken to determine the most forward position of the BM simulant within the diaper. This measurement consisted of measuring the distance between the rear waist edge of each article and the location of the BM simulant furthest from the rear waist edge of the article. This measurement helped to determine the performance of each article in preventing spreading of the BM simulant forward within the articles. The more forward the BM simulant spread, the more likely the BM simulant come into contact with sensitive areas of a wearer's skin. The results of this measurement are detailed below in Table 1. As can be seen, all of codes G, L, and J performed better than the control group, code K. As additionally can be seen, code L performed the best in preventing forward spread of the BM simulant, followed by code G, then code J.

A second measurement was taken measuring the overall spread of the BM simulant on the test articles. The reported results in Table 2 indicate the maximum distance between BM simulant located most rearward in a test article and BM simulant located most forward the test article. This measurement measured the performance of the articles in preventing overall spreading of the BM simulant, which is desirable to reduce exposure of the wearer's skin to BM and the skin irritants contained in the BM. Again, as can be seen, all of codes G, L, and J performed better than the control group, code K. Code L performed the best in preventing by having the lowest overall spread of BM, followed by code G, then code J.

A third measurement was taken measuring the minimum distance between the rear waist edge of each test article and the location of the most rearward BM simulant. This measurement indicates the performance of the test articles in preventing BM spreading toward the rear of the articles. Again, lower spreading of the BM is desirable in order to reduce the exposure of the wearer's skin to the BM. As can be seen from the data in Table 3, codes K, G, and L all performed somewhat similarly, while code L had a measurably higher performance.

TABLE 1

| | Maximum Forward Spread Distance of BM Simulant (in mm) | | | |
| --- | --- | --- | --- | --- |
| Code | Test 1 | Test 2 | Test 3 | Test 4 |
| K | 385 | 365 | 350 | 300 |
| G | 265 | 265 | 260 | 260 |
| L | 250 | 245 | 244 | 232 |
| J | 285 | 280 | 275 | 272 |

TABLE 2

| | Overall Spread of BM Simulant | | | |
| --- | --- | --- | --- | --- |
| Code | Test 1 | Test 2 | Test 3 | Test 4 |
| K | 320 | 295 | 255 | 250 |
| G | 224 | 201 | 200 | 197 |
| L | 178 | 175 | 172 | 170 |
| J | 230 | 227 | 222 | 200 |

TABLE 3

| | Minimum Distance of BM Simulant from Rear Edge of Article | | | |
| --- | --- | --- | --- | --- |
| Code | Test 1 | Test 2 | Test 3 | Test 4 |
| K | 47 | 52 | 55 | 63 |
| G | 46 | 55 | 58 | 60 |
| L | 60 | 67 | 70 | 76 |
| J | 55 | 57 | 57 | 65 |

Taking all of Tables 1-3 into consideration, it can be seen that the code L test articles, the articles that had the rear edge of the secondary liner sheet located 230 mm from the rear waist edge of the article, performed the best. Additionally, the code G test articles, the articles that had the rear edge of the secondary liner sheet located 242 mm from the rear waist edge of the articles performed better than the code J test articles, which were the test articles that had the rear edge of the secondary liner sheet located 255 mm from the rear waist edge of the articles. Additionally, all of the codes L, G, and J performed better than the control.

Accordingly, the precise location of the rear sheet edge of the secondary liner material is a key feature affecting performance of the absorbent articles including a secondary liner sheet. Therefore, in embodiments of the present disclosure it may be preferred that the rear edge 211 of the secondary liner sheet 201 is located between about 220 mm and about 254 mm from the rear waist edge 24 of article 10 where article 10 has an overall length 225 of about 445 mm, or between about 225 mm and about 245 mm in other embodiments. Of course, where article 10 has other values for overall length 225, it may be preferred that the rear edge 211 of the secondary liner sheet 201 is located in approximately the same relative position as where the article 10 has an overall length 225 of about 445 mm. For instance, it may be preferred that the rear edge 211 of the secondary liner sheet 201 is located a distance from the rear waist edge 24 of the article 10 between about 49% and about 57% of the overall length 225 of the article 10. In other embodiments, it may be preferred that the rear edge 211 of the secondary liner sheet 201 is located a distance from the rear waist edge 24 of the article 10 between about 52% and about 55% of the overall length 225 of the article 10.

FIG. 4 is a cross-section view of article 10 as viewed along line 4-4 in FIG. 2. As can be seen, FIG. 4 is from the perspective of the front of article 10 looking toward the rear waist region 14. Additionally as can be seen, the article 10 is shown in a relaxed state where the containment flaps 50, 52 are extending away from the body facing surface 19 of the chassis 11. Accordingly, as the secondary liner sheet 201 is attached to at least a portion of the containment flaps 50, 52, a portion of the secondary liner sheet 201 is also shown pulled away from the body facing surface 19 forming pocket 228.

FIG. 4 depicts the secondary liner sheet 201 bonded to the containment flaps 50, 52 with two alternative bond types to illustrate how the structure of the different bond types may differ. With respect to containment flap 50, the secondary liner sheet 201 is bonded to the containment flap 50 through attachment regions 230. As can be seen, attachment regions 230 are located in specific locations in relation to the containment flap 50, as the depicted attachment regions 230 comprise point-fusion bonds. The bond regions 230 are shown un-aligned with flap elastics 68. Accordingly, in at least some embodiments, the attachment regions 230 may not overlap any of the flap elastics 68. This relationship between the attachment regions 230 and the flap elastics 68 may be chosen so as to provide secure attachment of the secondary liner sheet 201 to the containment flap 50 while avoiding severing the flaps elastics 68 during the attachment process to form the attachment regions 230. Additionally, although not shown, in some embodiments, the secondary liner sheet 201 may be attached to the containment flap 50 with another attachment region 230 that coincides with the distal edge 65b of the containment flap 50. The point-fusion bonds of the attachment regions 230 may be formed through pressure bonding, ultrasonic bonding, and/or heat bonding, or any other suitable type of forming point-fusion bonds.

FIG. 4 further depicts the secondary liner sheet 201 attached to containment flap 52 through attachment region 232. As can be seen, the attachment region 232 may spread between the distal edge 65b of containment flap 52, or proximate the distal edge 65b without being disposed at the distal edge 65b, and a medial portion of the containment flap 52, providing a large bonding area between the secondary liner sheet 201 and the containment flap 52. The attachment region 232 may comprise an adhesive which attaches the secondary liner sheet 201 to the containment flap 52. It should be understood that, in general, the secondary liner sheet 201 may be bonded to both containment flaps 50, 52 by the same type of bonds, and that FIG. 4 is depicted with different types of bonds as an example only.

In at least some embodiments, an edge of the attachment region 232 of FIG. 4, which may be a particular embodiment of flap attachment regions 205a, 205b described with respect to other figures, may not align with the distal edge 65b of the containment flaps 50, 52. For instance, it can be seen in FIG. 4 that an edge of the attachment region 232 most proximate the distal edge 65b is spaced some amount from the distal edge 65b. As can be seen more clearly in FIG. 3, in at least some embodiments, the attachment regions attaching the secondary liner sheet 201 to the containment flaps 50, 52, for example attachment regions 205a, 205b, may be spaced from the distal edge 65b of the containment flaps 50, 52 a distance 273. The distance 273 may be between about 0 mm and about 30 mm, or between about 1 mm and about 25 mm, or may be about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm, or any other suitable value.

The attachment between the secondary liner sheet 201 and the containment flaps 50, 52, e.g. attachment regions 205a, 205b, may further define a secondary liner attachment height 271 of the secondary liner 201. The secondary liner attachment height 271 may generally describe a height that the secondary liner sheet 201 may achieve above the liner 28. Although the exact height that the secondary liner sheet 201 may achieve during use will vary depending on a particular wear state of the article 10, such possible heights may still be related to the secondary liner attachment height 271. The secondary liner attachment height 271 is defined as the distance between the attachment region of the containment flaps 50, 52 and the liner 28, e.g. longitudinally extending attachment regions 49, and an edge of the attachment regions 205a, 205b most proximate the distal edges 65b of the containment flaps 50, 52. The height that the secondary liner sheet 201 may achieve during use may generally fall within the range of about plus or minus 20% of the secondary liner attachment height 271, as the side portions of the chassis 11, containing the attachment regions 49, may move above or below the plane of the absorbent body 34 in different wear configurations.

In some embodiments, it may be beneficial to choose the rear un-bonded length 214 of the secondary liner sheet 201 in relation to the flap attachment height 271 and/or the longitudinal bond length 212 of the flap attachment bonds 205a, 205b. For instance, in some embodiments, it may be beneficial to ensure that the rear un-bonded length 214 is greater than the secondary liner attachment height 271. In other embodiments, the rear un-bonded length 214 may be greater than the sum of the longitudinal bond length 212 and half of the secondary liner attachment height 271. In still further embodiments, the rear un-bonded length 214 may be greater than the sum of the longitudinal bond length 212 and 80% of the secondary liner attachment height 271. These embodiments may ensure that the pocket 228 is long enough to adequately contain BM exudates. Additionally, it may be beneficial in some embodiments that the rear un-bonded length 214 is not too long. For instance, in some embodiments it may be beneficial for the rear un-bonded length 214 to be less than the sum of the longitudinal bond length 212 and one and a half times the secondary liner attachment height 271. In further embodiments, the rear un-bonded length 214 may be less than the sum of the longitudinal bond length 212 and 120% of the secondary liner attachment height 271.

Figure 5:
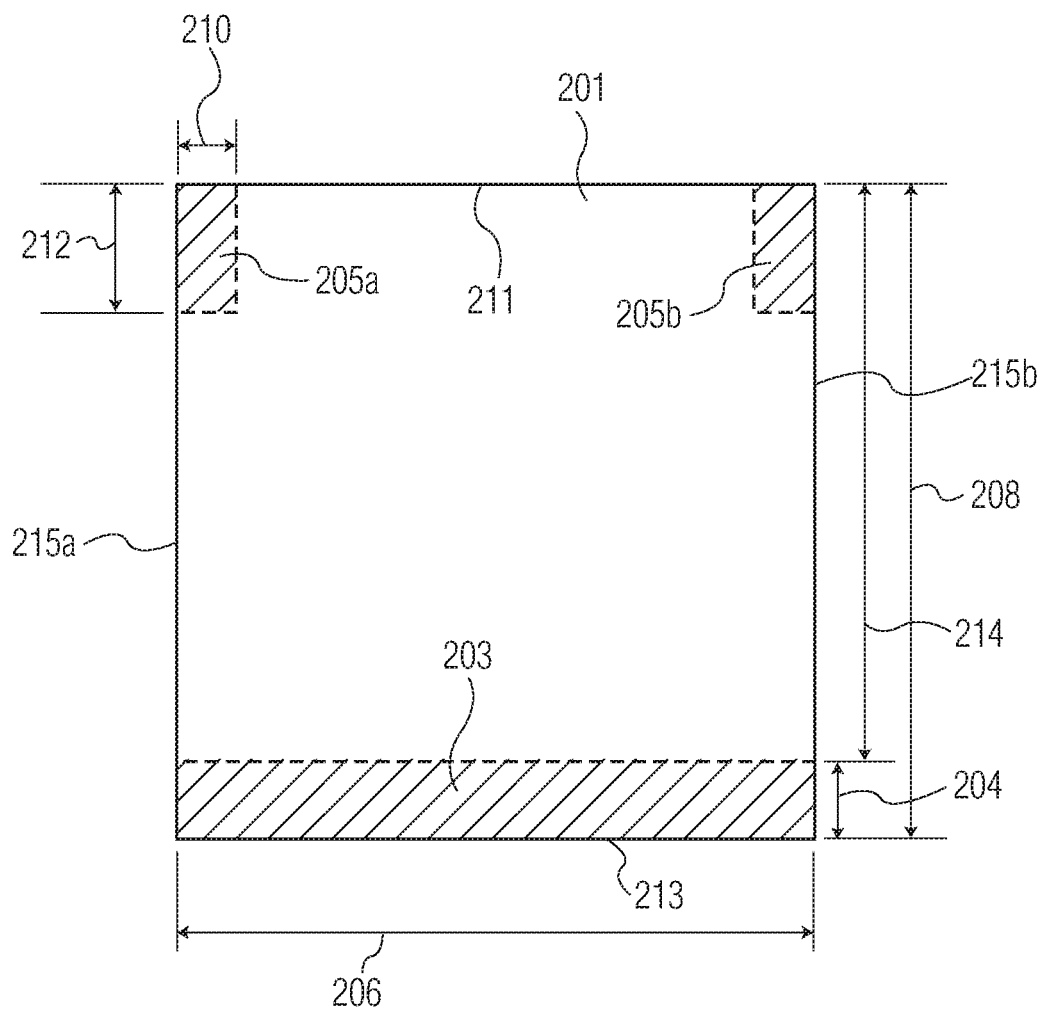
FIG. 5 is a top plan view of the secondary liner sheet of FIG. 2, according to aspects of the present disclosure.

FIG. 5 is a plan view of the secondary liner sheet 201 separate from article 10, including regions indicating locations of the liner attachment bond 203 and the flap attachment bonds 205a, 205b. Generally, the secondary liner sheet 201 may be made from any of a number of suitable materials. For example, the secondary liner sheet 201 may be made from any material listed above with respect to liner 28. In some specific embodiments, the secondary liner sheet 201 may be a dual-layer hydroentangled material such as that described in U.S. Pat. No. 9,474,660, titled "Absorbent Article", the entirety of which is herein incorporated by reference. In at least some specific embodiments, the secondary liner sheet 201 may generally range in basis weight between about 20 gsm and about 50 gsm, or between about 25 gsm and about 35 gsm. These basis weight ranges were found to prevent seepage of BM exudates through the secondary liner sheet 201 where such a feature is desired. In a further embodiment, a secondary liner sheet 201 can be a spunbond substrate with a basis weight from about 8 to about 40 gsm. In an embodiment, a secondary liner sheet 201 can be a 10 gsm spunbond-meltblown-spunbond substrate having 20% meltblown content applied between the two spunbond layers.

Additionally, in at least some embodiments, the secondary liner sheet 201 may be formed from a hydrophilic material, or a hydrophobic material that has been treated to become hydrophilic. This hydrophilic nature may help with uptake of liquid insults, thereby drawing the liquids away from a wearer's skin, and transferring the liquids to other components of the article 10, such as the liner 28 which may be further suited to uptake and distribution of the liquid throughout the article 10 to move the liquid away from the wearer's skin and lock it within the article 10.

The secondary liner sheet 201 may have an elastic behavior such that it may be significantly elastically extensible during the process of making the absorbent article 110 or 10, and during application of the absorbent article 110 or 10 on the wearer, whilst providing in in-use conditions (during wear) correct alignment with the skin of the wearer, both when the wearer moves the legs apart and when the wearer moves the legs together.

Figure 5A:
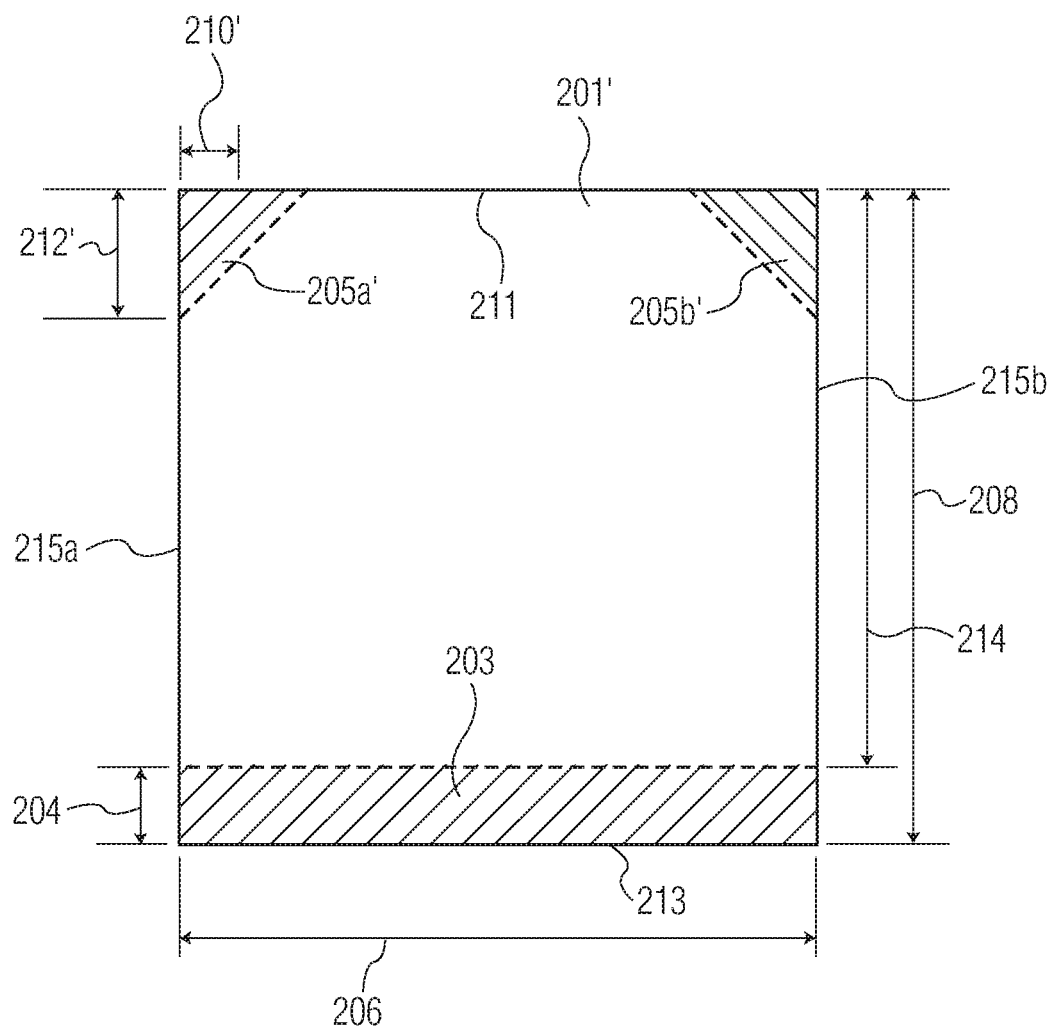
FIG. 5A is a top plan view of the secondary liner sheet of FIG. 2 including alternative bond locations.

FIG. 5A is a plan view of an alternative secondary liner sheet 201' including alternative flap attachment bonds 205a', 205b' shapes. In the embodiment of FIG. 5A, the flap attachment bonds 205a', 205b' may have lateral bond widths 210' and longitudinal bond lengths 212'. In general, the lateral bond widths 210' and longitudinal bond lengths 212' may have similar values to the lateral bond widths 210 and longitudinal bond lengths 212 of the secondary liner sheet 201. However, in the embodiment of FIG. 5A, the flap attachment bonds 205a', 205b' may have a triangular shape instead of a rectangular or square shape. However, it should be understood that in different embodiments, the flap attachment bonds 205a, 205b, 205a', 205b' could have any suitable shape.

As described previously, the flap attachment bonds 205a, 205b, and now 205a', 205b', could represent any suitable bonds—for instance, adhesive bonds, ultrasonic bonds, pressure bonds, heat bonds, and the like. It should be understood that in further embodiments, the specific pattern of the bonds within the flap attachment bonds 205a, 205b, 205a', 205b' may vary. For example, where the flap attachment bonds 205a, 205b, 205a', 205b' are adhesive bonds, adhesive may be spread over the whole of flap attachment bonds 205a, 205b, 205a', 205b'. However, where the flap attachment bonds 205a, 205b, 205a', 205b' are pressure bonds, each of the flap attachment bonds 205a, 205b, 205a', 205b' may contain point-fusion bonds which do not occupy the entire area of the flap attachment bonds 205a, 205b, 205a', 205b'. As some examples where the flap attachment bonds 205a, 205b, 205a', 205b' represent pressure bonds, the total bonded area with each of the flap attachment bonds 205a, 205b, 205a', 205b' may range between about 20% to about 60%.

Figure 6:
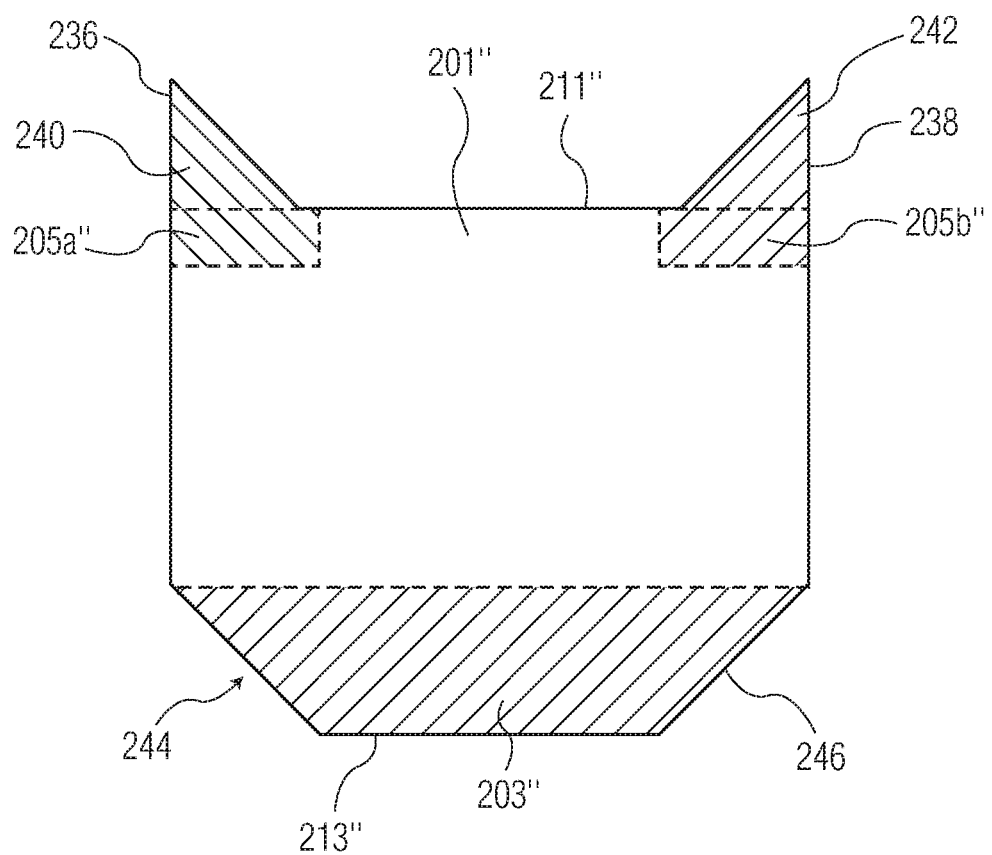
FIG. 6 is a top plan view of an alternative secondary liner sheet, according to aspects of the present disclosure.

FIG. 6 is a plan view of an alternative exemplary secondary liner sheet 201" having an alternative shape to secondary liner sheet 201. In the embodiment of FIG. 6, the secondary liner sheet 201" may additionally have ear portions 236, 238 proximate rear sheet edge 211" and recessed portions proximate front sheet edge 213". The ear portions 236, 238 may generally extend rearward of rear sheet edge 211". Although ear portions 236, 238 are shown as triangular, it should be understood that the ear portions 236, 238 could have any suitable shape, such as a rectangle or trapezoid, as a few non-limiting examples. In at least some embodiments, the secondary liner sheet 201" may be attached to the containment flaps 50, 52 through ear portions 236, 238. Accordingly, in such embodiments, ear portions 236, 238 may comprise bonds 240, 242, which may be any suitable type of bonds—such as any of those described herein. In some of these embodiments, the secondary liner sheet 201" may still comprise the flap attachment bonds 205a", 205b", although in other embodiments, the flap attachment bonds 205a", 205b" may be omitted. The recessed portions 244, 246 may cause the liner attachment bond 203 " to have a trapezoidal shape, although in other embodiments, the recessed portions 244, 246 may differ in their shape, which may give the liner attachment bond 203" a different shape as well.

Figure 7:
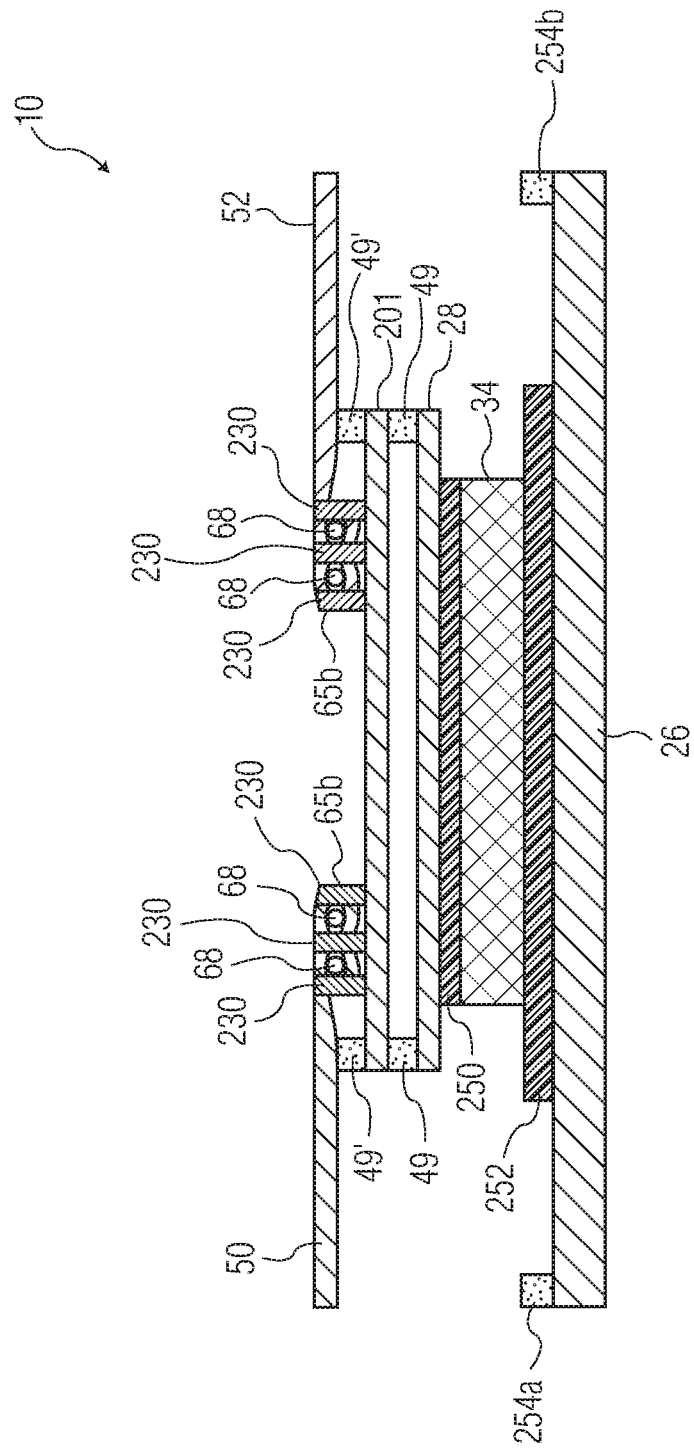
FIG. 7 is a cross-section schematic view of the absorbent article of FIG. 3 as viewed along line 7-7.
Figure 8:
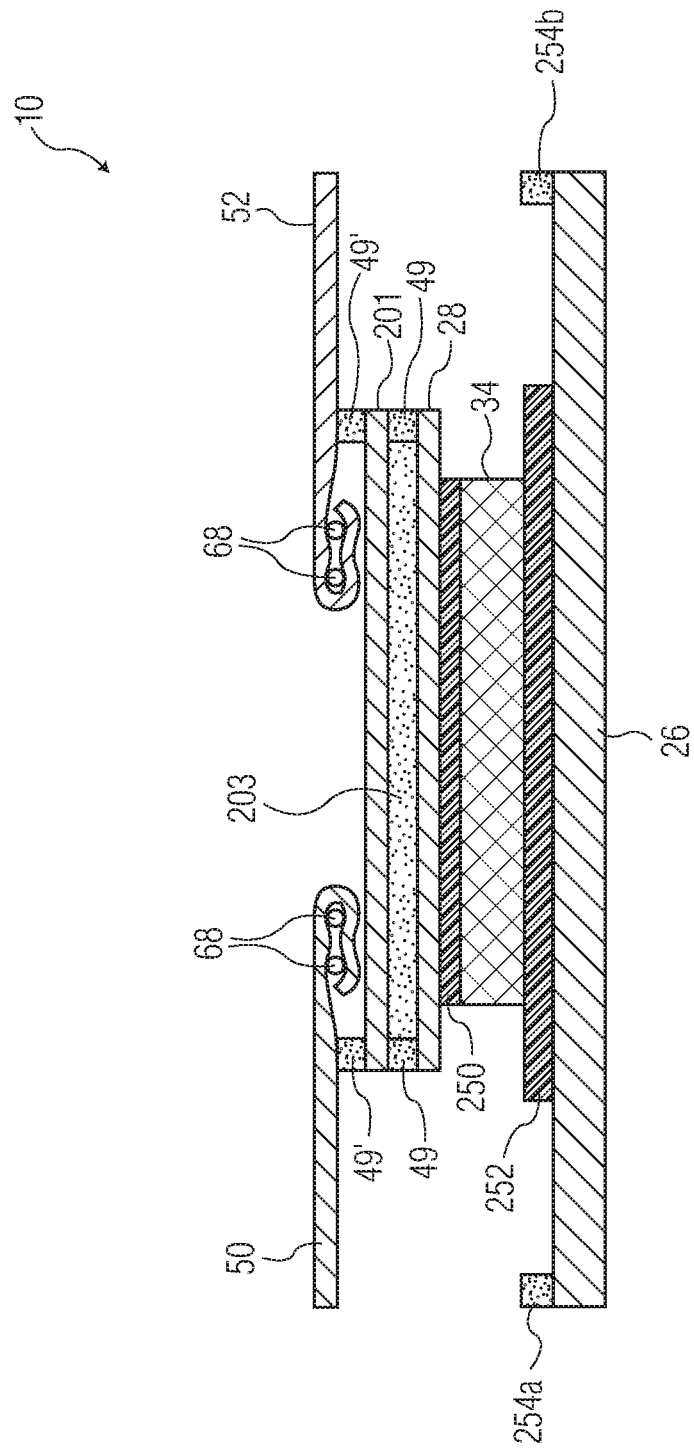
FIG. 8 is a cross-section schematic view of the absorbent article of FIG. 3 as viewed along line 8-8.

FIGS. 7 and 8 are cross-section schematic views showing the different layers within article 10 as viewed along lines 7-7 and 8-8 in FIG. 3, respectively. In the embodiments of FIGS. 7 and 8, the secondary liner sheet 201 is attached to the containment flaps 50, 52 through attachment regions 230. As seen in FIG. 7, article 10 includes the outer cover layer 26 bonded to the absorbent body 34 through adhesive layer 252. The outer cover 26 may further include attachment regions 254a, 254b, which may help to secure the containment flaps 50, 52, or the liner 28 in other embodiments, to the outer cover 26.

Article 10 further includes liner 28 bonded to the absorbent body 34 through adhesive layer 250. On top of the liner 28, the secondary liner sheet 201 is bonded to the liner 28 through the first attachment regions 49. In articles without the secondary liner sheet 201, or portions of the article 10 where the secondary liner sheet 201 is not present, or where the secondary liner sheet 201 has a lateral sheet width 206 that is less than distance between the first attachment regions 49, the containment flaps 50, 52 are bonded directly to the liner through the first attachment regions 49. In the embodiment shown in FIG. 7, however, the secondary liner sheet 201 extends all the way between the first attachment regions 49. Accordingly, the first attachment regions 49 attach the liner 28 to the containment flaps 50, 52 in regions of the article 10 where the secondary liner sheet 201 is not present and the liner 28 to the secondary liner sheet 201 in regions of the article 10 where the secondary liner sheet 201 is present. In such embodiments, second attachment regions 49' may be formed to attach the secondary liner sheet 201 to the containment flaps 50, 52. Each of the first attachment regions 49 and the second attachment regions 49' may be formed from any suitable attachment means, for instance with one or more adhesives, with pressure bonds, with ultrasonic bonds, with bonds formed through heat, or the like.

In some embodiments, the second attachment regions 49' may extend for a length in the longitudinal direction 30 of the article 10 equal to the longitudinal length 208 of the secondary liner sheet 201. In other embodiments, the second attachment regions 49' may extend for a length in the longitudinal direction 30 of the article 10 equal to anywhere between about 50% and about 100% the longitudinal length 208. Although shown as generally extending parallel to each other, in other embodiments, the first attachment regions 49 and the second attachment regions 49' may not be parallel. For instance, the first attachment regions 49 may extend in a generally longitudinal direction, for example in a direction that is generally parallel to the longitudinal centerline 29, while the second attachment regions 49' extend in a direction forming an angle with respect to the longitudinal centerline 29. Such an angle may be between about 5 degrees and about 35 degrees, or between about 5 degrees and about 25 degrees, or between about 5 degrees and about 10 degrees. In still further embodiments, the angle may be between about 1 degree and about 5 degrees.

Additionally as can be seen in FIG. 7, there are three separate attachment regions 230 attaching the secondary liner sheet 201 to the containment flaps 50, 52. In the embodiment of FIG. 7, three separate "lines" of point-fusion bonds 230 are depicted attaching the secondary liner sheet 201 to the each containment flaps 50, 52. It should be understood that this number is only for illustration—in other embodiments, the number of point-fusion bonds could be different, such as anywhere between 1 and 10. In still further embodiments, the containment flaps 50, 52 may be attached to the secondary liner sheet 201 with adhesive, as opposed to point fusion bonds, as described with respect to FIG. 4. However, in the example of FIG. 7, it can be seen that none of the attachment regions 230 overlap the flap elastics 68. In at least some embodiments, one of the attachment regions 230 lines may coincide with distal edge 65b of the containment flaps 50, 52.

In FIG. 8, there are no bonds shown attaching the containment flaps 50, 52 to the secondary liner sheet 201, because in the region of the article 10 bisected by line 8-8, there is no attachment between the containment flaps 50, 52 and the secondary liner sheet 201. Instead, the region of the article 10 shown in FIG. 8 is where the secondary liner sheet 201 is attached to the liner 28. Accordingly, as can be seen in contrast to FIG. 7, FIG. 8 further includes liner attachment bond 203, extending between first attachment regions 49 attaching the secondary liner sheet 201 to the liner 28.

Figure 9:
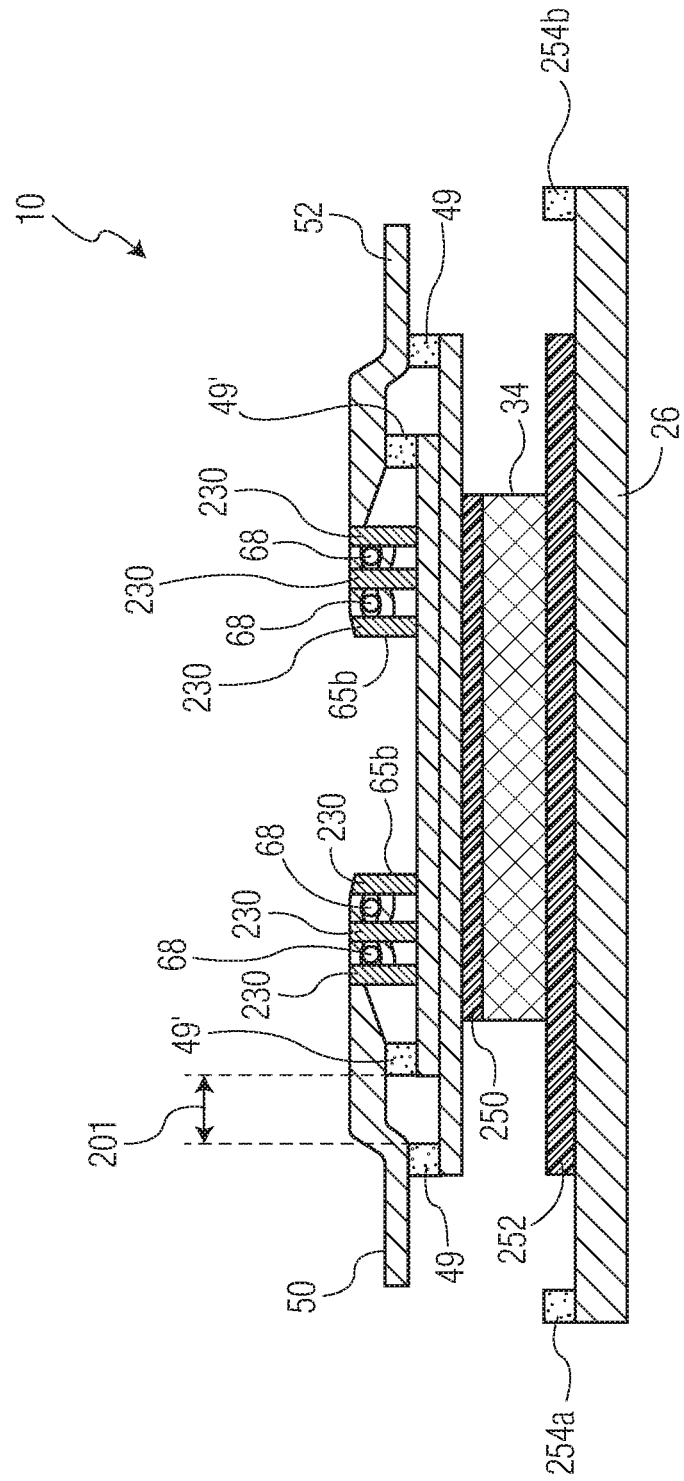
FIG. 9 is a side view of an absorbent article according to an embodiment of the present invention in flat state.
Figure 10:
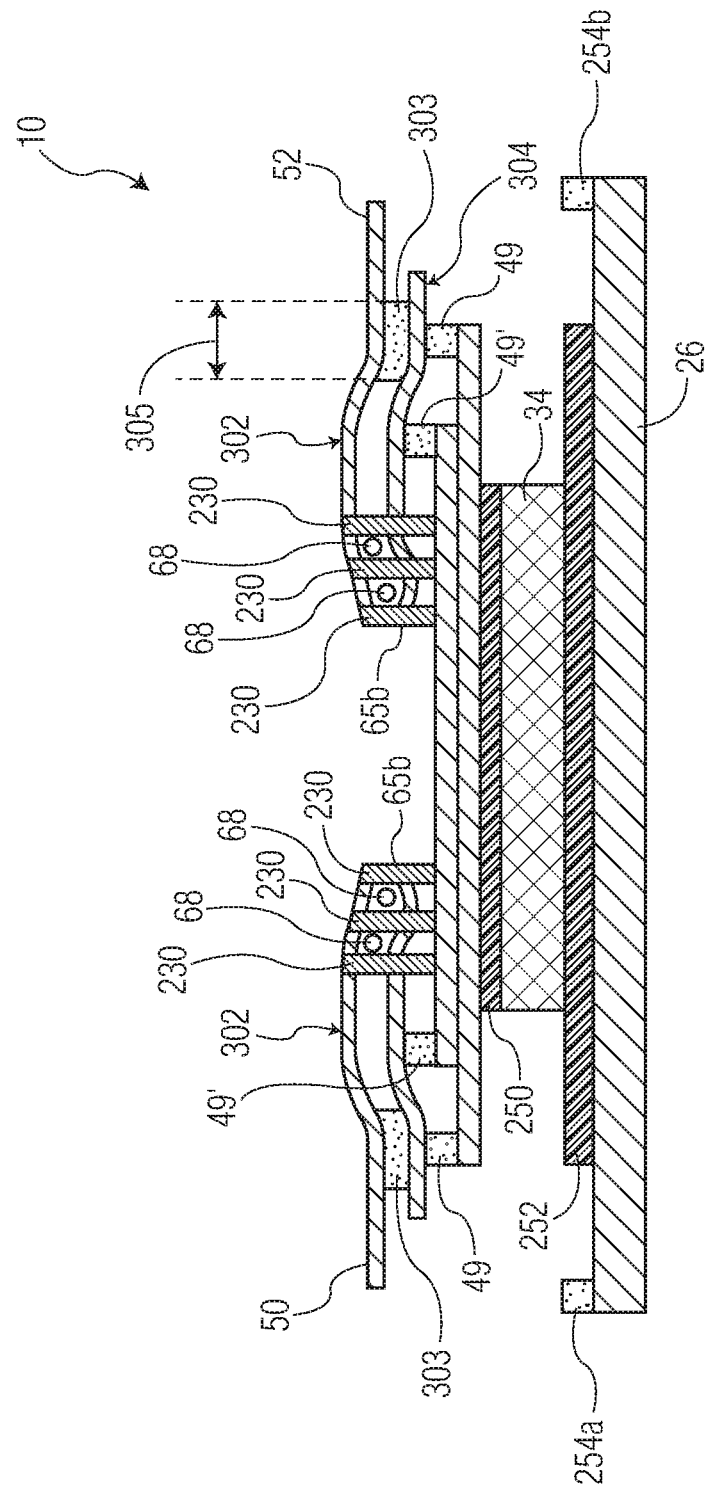
FIG. 10 is a side view of an absorbent article in flat state according to an embodiment of the present invention.

FIGS. 9 and 10 depict cross-sections of alternative embodiments of absorbent article 10 of the present disclosure as viewed along line 7-7 of FIG. 3. In some embodiments, it may be desirable that the secondary liner sheet 201 is narrower than (has a sheet width 206 that is less than) the distance between the attachment points of containment flap 50 and containment flap 52 to the chassis 11, e.g. the first attachment regions 49. For instance, in some embodiments the secondary liner sheet 201 may be hydrophilic and in such embodiments, if the secondary liner sheet 201 is as wide as or wider than the distance between the first attachment regions 49, the article 10 may leak as the secondary liner sheet 201 may absorb bodily exudates and wick the exudates underneath and laterally outside of the confines of the containment flaps 50, 52. In such embodiments, the first attachment regions 49 and the second attachment regions 49' may be staggered in relation to each other in the vertical direction 33, as shown in FIGS. 9 and 10.

Figure 11:
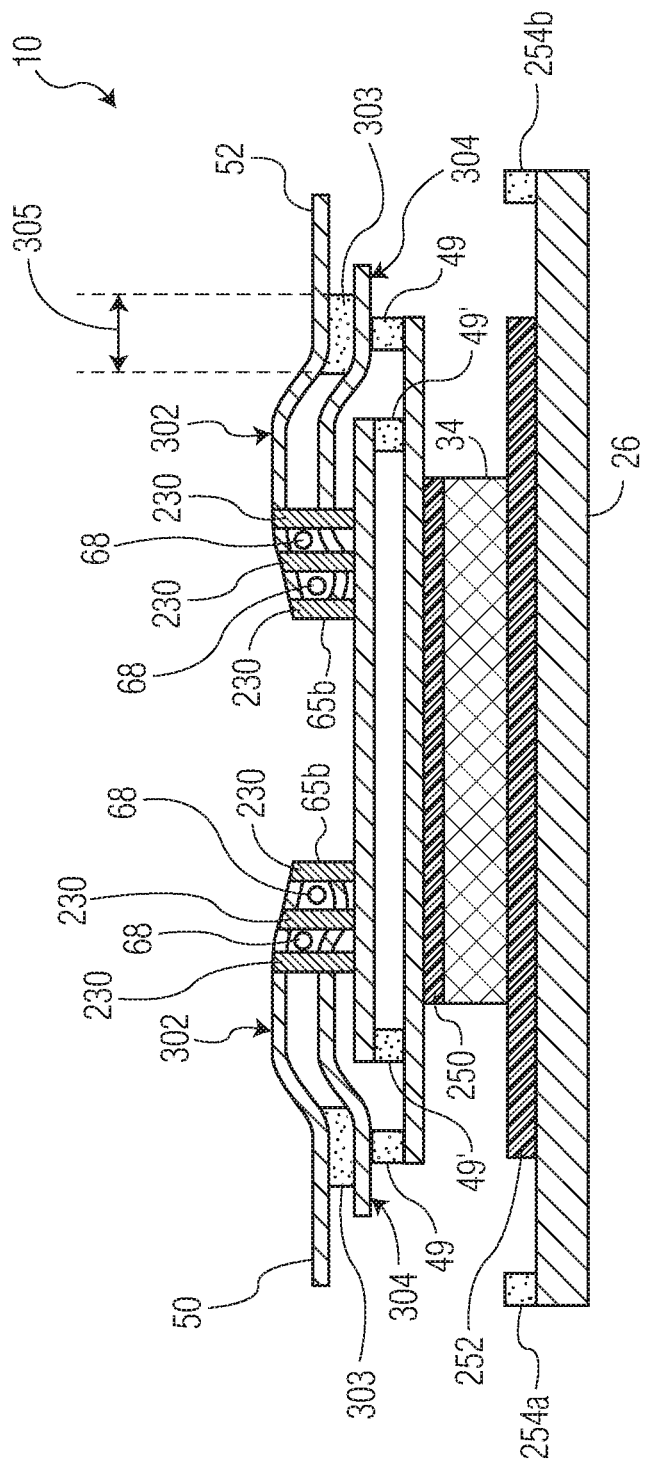
FIG. 11 is a side view of an absorbent article in flat state according to an embodiment of the present invention.

FIGS. 9 and 10, show the first attachment regions 49 attaching the secondary liner sheet 201 to the containment flaps 50, 52 and the first attachment regions 49 attaching the liner 28 to the containment flaps 50, 52. However, in other embodiments, such as that shown in FIG. 11, the second attachment regions 49' may instead attach the secondary liner sheet 201 to the liner 28 as opposed to the containment flaps 50, 52. Additionally, as can be seen in all of FIGS. 9-11, the first attachment regions 49 and the second attachment regions 49' may be staggered in relation to each other in the vertical direction 33 such that there is no overlap between the first attachment regions 49 and the second attachment regions 49' in the vertical direction 33. For instance, the first attachment regions 49 and the second attachment regions 49' may be spaced from each other by an attachment region spacing 301. The attachment region spacing 301 may range between about 0.5 mm to about 20 mm in various embodiments, between about 1 mm and about 15 mm in other embodiments, between about 1 mm and about 10 mm in other embodiments, between about 1 mm and about 5 mm in other embodiments, or any specific value within any of these disclosed ranges.

In at least some of these embodiments, the first attachment regions 49 may be spaced outboard of the second attachment regions 49', as shown in FIGS. 9 and 10. That is, the first attachment regions 49 may be located closer to the side edges 18, 20 of the chassis 11 than the second attachment regions 49'. In an alternative description, the second attachment regions 49' may be located closer to a longitudinal centerline of the article 10 than the first attachment regions 49. This configuration may provide one or more benefits, particularly when the secondary liner sheet 201 is hydrophilic. For instance, in such configurations, the first attachment regions 49 attaching the liner 28 to the containment flaps 50, 52 may provide a liquid-impermeable seal between the liner 28 and the containment flaps 50, 52. When a liquid insult occurs, even if the secondary liner sheet 201 is hydrophilic and absorbs and wicks some of the liquid, because the secondary liner sheet 201 is contained within the lateral bounds of the containment flaps 50, 52, e.g. between the first attachment regions 49, the liquid impermeability of the attachment of the liner 28 to the containment flaps 50, 52 through the first attachment regions 49 ensures that none of the insulted liquid can escape past the containment flaps 50, 52 through the first attachment regions 49.

Although shown as generally similar, it not necessarily the case that the attachment regions 49, 49' need to be the same. For instance, the thickness of the attachment regions 49, 49' in the vertical direction 33 may differ in some embodiments. In additional or alternative embodiments, attachment regions 49, 49' may comprise different types of bonds, for instance any combination of pressure, heat, ultrasonic, adhesive, or other conventional bonds. In at least some embodiments, the attachment regions 49, 49' both comprise adhesive bonds. In such embodiments, the second attachment regions 49' may comprise an adhesive that forms a liquid impermeable barrier between the liner 28 and the containment flaps 50, 52 while the first attachment regions 49 may comprise an adhesive that may or may not form a liquid impermeable barrier between the secondary liner sheet 201 and the containment flaps 50, 52.

A further feature shows each containment flap 50, 52 may contain an un-folded portion 302 and a folded portion 304, as detailed in FIG. 10, wherein at least part of the folded portion 304 overlaps the unfolded portion 302 in the vertical direction 33. Further, the folded portions 304 may only overlap the unfolded portions 302 of the containment flaps 50, 52 in board of the first attachment regions 49 in some embodiments, while overlapping the unfolded portions 302 both inboard and outboard of the first attachment regions 49 in other embodiments, thereby extending beyond the edges of the secondary liner sheet 201. In still further embodiments, the folded portions 304 may overlap the unfolded portions 302 of the containment flaps 50, outboard even of the second attachment regions 49' in other embodiments In at least some embodiments where the containment flaps 50, 52 include un-folded portions 302 and folded portions 304, a bond 303 may attach the folded portions 304 and unfolded portions 302 of the containment flaps 50, 52. The bonds 303 may comprise an adhesive in some embodiments, while in other embodiments the bonds 303 may comprise ultrasonic bonds, thermal bonds, pressure bonds, or any other type of conventional bonds. The bonds 303 may comprise a bond width 305, as seen in FIG. 10, which extends in the lateral direction 302. The bond width 305 may range from about 0.5 mm to about 5 mm.

In at least some embodiments of the present disclosure, the second attachment regions 49' may vertically overlap the bonds 303. Such embodiments may be one way to ensure a liquid-impermeable barrier is created between the liner 28 and the containment flaps 50, 52. For instance, the overlapping of the bonds of the second attachment regions 49' and the bonds 303 may form a liquid-impermeable barrier such that liquid cannot escape past the second attachment regions, even in embodiments where the containment flaps 50, 52 comprise a hydrophilic material.

In additional or alternative embodiments to the above embodiments which include the adhesive 303, and in which the adhesive 303 and the second attachment regions 49' vertically overlap, the material comprising the containment flaps 50, 52 may be greater than about 16 gsm. Such thickness in the material of the containment flaps 50, 52 may additionally help to prevent liquid from escaping past the containment flaps 50, 52, as the density and bulk of such a material may be enough to prevent liquid seeping through the material. Alternatively or additionally to utilizing a material that has a basis weight greater than about 16 gsm, the material may be further treated to be hydrophobic. For instance, a hydrophobic agent may be applied to the material comprising the containment flaps 50, 52 in order to make the containment flaps 50, 52 hydrophobic, and thereby increase the ability of the containment flaps 50, 52 to prevent seepage of liquid through the containment flaps 50, 52 and outside of the bounds of the second attachment regions 49'.

In view of FIG. 10, the containment flap fold over may increase over 20% from about 40 mm to about 55 mm. And the flap width may increase over at least 10% from about 290 mm to about 310 mm.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. An absorbent article comprising:
    a chassis extending in a longitudinal direction and having a longitudinal centerline and a lateral direction and having a lateral centerline, the chassis having a front waist region including a front waist edge, a rear waist region including a rear waist edge, and a crotch region extending between the front waist region and the rear waist region, and the chassis comprising:
    a garment facing outer cover,
    a body facing liner,
    an absorbent body disposed between the garment facing outer cover and the body facing liner;
    a pair of containment flaps extending between the front waist region and the rear waist region, each of the pair of containment flaps having distal edges and proximal edges; and
    a secondary liner sheet having a rear sheet edge, a front sheet edge, and longitudinally extending sheet side edges,
    wherein the secondary liner sheet is attached to each of the containment flaps along flap attachment regions disposed proximate the distal edges, each of the flap attachment regions having a flap attachment region length and a flap attachment region height,
    wherein each of the flap attachment regions has a flap attachment region length, and
    wherein each of the flap attachment region lengths is between about 8% and about 16% of a total length of the absorbent article; and
    wherein the secondary liner is attached to the body-facing liner through a liner attachment region and has a rear un-bonded region extending between the liner attachment region and the rear sheet edge, the rear un-bonded region has a rear un-bonded region length, and
    wherein the rear un-bonded region length is greater than the flap attachment height, the flap attachment height being defined as a distance between one of the first longitudinally extending attachment regions and an edge of a flap attachment region most proximate a distal edge of a containment flap.

2. The absorbent article of claim 1, wherein the flap attachment region lengths are the same.

3. The absorbent article of claim 1, wherein the secondary liner sheet is attached to each of the pair of containment flaps along longitudinally extending attachment regions disposed proximate the proximal edges.

4. The absorbent article of claim 3, wherein the longitudinally extending attachment regions disposed proximate the proximal edges are second longitudinally extending attachment regions, and wherein each of the pair of containment flaps are attached to the body facing liner along first longitudinally extending attachment regions disposed proximate the proximal edges.

5. The absorbent article of claim 4, wherein the second longitudinally extending attachment regions are disposed laterally closer to the longitudinal centerline than the first longitudinally extending attachment regions.

6. An absorbent article comprising:
    a chassis extending in a longitudinal direction and having a longitudinal centerline and a lateral direction and having a lateral centerline, the chassis having a front waist region including a front waist edge, a rear waist region including a rear waist edge, and a crotch region extending between the front waist region and the rear waist region, and the chassis comprising:
    a garment facing outer cover,
    a body facing liner,
    an absorbent body disposed between the garment facing outer cover and the body facing liner;
    a pair of containment flaps extending between the front waist region and the rear waist region, each of the pair of containment flaps having distal edges and proximal edges; and
    a secondary liner sheet having a rear sheet edge, a front sheet edge, and longitudinally extending sheet side edges, wherein each of the pair of containment flaps are attached to the body facing liner along first longitudinally extending attachment regions disposed proximate the proximal edges, wherein the secondary liner sheet is attached to each of the containment flaps along flap attachment regions disposed proximate the distal edges, each of the flap attachment regions having a flap attachment region length and a flap attachment region height, the flap attachment region height being defined as a distance between one of the first longitudinally extending attachment regions and an edge of a flap attachment region most proximate a distal edge of a containment flap, wherein the secondary liner sheet is attached to the body facing liner through a liner attachment region and has a rear un-bonded region extending between the liner attachment region and the rear sheet edge, the rear un-bonded region having a rear un-bonded region length, and wherein the rear un-bonded region length is greater than the flap attachment region height.

7. The absorbent article of claim 6, wherein the rear un-bonded region is at least greater than 50% of the flap attachment region height plus the length of the attachment.

8. The absorbent article of claim 6, wherein the rear un-bonded region length is greater than the sum of flap attachment region length and 50% of the flap attachment region height.

9. The absorbent article of claim 8, wherein the rear un-bonded region length is less than the sum of the flap attachment region length and 150% of the flap attachment region height.

10. The absorbent article of claim 6, wherein the rear un-bonded region length is greater than the sum of the flap attachment region length and 80% of the flap attachment region height.

11. The absorbent article of claim 10, wherein the rear un-bonded region length is less than the sum of the flap attachment region length and 120% of the flap attachment region height.

12. An absorbent article comprising:
a chassis extending in a longitudinal direction and having a longitudinal centerline and a lateral direction and having a lateral centerline, the chassis having a front waist region including a front waist edge, a rear waist region including a rear waist edge, and a crotch region extending between the front waist region and the rear waist region, and the chassis comprising:
a garment facing outer cover,
a body facing liner,
an absorbent body disposed between the garment facing outer cover and the body facing liner;
a pair of containment flaps extending between the front waist region and the rear waist region, each of the pair of containment flaps having distal edges and proximal edges; and
a secondary liner sheet having a rear sheet edge, a front sheet edge, and longitudinally extending sheet side edges, wherein the secondary liner sheet is attached to the body facing liner through a liner attachment region, the liner attachment region having a liner attachment region front edge and a liner attachment region rear edge, wherein the secondary liner sheet is attached to each of the containment flaps along flap attachment regions disposed proximate the distal edges, each of the flap attachment regions having a flap attachment region length and a flap attachment region height, wherein the liner attachment rear edge is disposed away from the front waist edge a distance greater than about 40% of a total length of the absorbent article; and wherein the secondary liner is attached to the body-facing liner through a liner attachment region and has a rear un-bonded region extending between the liner attachment region and the rear sheet edge, the rear un-bonded region has a rear un-bonded region length, and wherein, the rear un-bonded region length is greater than the flap attachment height.

13. The absorbent article of claim 12, wherein the liner attachment rear edge is disposed away from the front waist edge a distance greater than about 35% of the total length of the absorbent article.

14. The absorbent article of claim 12, wherein the liner attachment rear edge is disposed away from the front waist edge a distance greater than about 25% of the total length of the absorbent article.

15. The absorbent article of claim 12, wherein the liner attachment region has a liner attachment region length extending between the liner attachment region front edge and the liner attachment region rear edge, and wherein the liner attachment region length is between about 1% and about 15% of the total length of the absorbent article.

16. The absorbent article of claim 12, wherein the liner attachment region has a liner attachment region length extending between the liner attachment region front edge and the liner attachment region rear edge, and wherein the liner attachment region length is between about 5% and about 15% of the total length of the absorbent article.

17. The absorbent article of claim 12, wherein the secondary liner sheet is hydrophilic.

18. The absorbent article of claim 12, wherein the liner attachment region is hydrophilic.

* * * * *